(12) United States Patent
Smith et al.

(10) Patent No.: US 7,820,687 B2
(45) Date of Patent: Oct. 26, 2010

(54) PYRIMIDINYL SULFONAMIDE COMPOUNDS WHICH INHIBIT LEUKOCYTE ADHESION MEDIATED BY VLA-4

(75) Inventors: Jenifer Smith, South San Francisco, CA (US); Chris Semko, Fremont, CA (US); Ying-Zi Xu, Palo Alto, CA (US); Andrei W. Konradi, Burlingame, CA (US)

(73) Assignee: Elan Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 12/505,383

(22) Filed: Jul. 17, 2009

(65) Prior Publication Data

US 2010/0016345 A1 Jan. 21, 2010

Related U.S. Application Data

(63) Continuation of application No. 11/679,042, filed on Feb. 26, 2007, now Pat. No. 7,579,466.

(60) Provisional application No. 60/777,595, filed on Feb. 27, 2006.

(51) Int. Cl.
*A61K 31/506* (2006.01)
*A61P 1/06* (2006.01)
*A61P 11/06* (2006.01)
*A61P 19/02* (2006.01)
*A61P 25/14* (2006.01)
*A61P 35/04* (2006.01)
*A61P 37/06* (2006.01)
*C07D 239/50* (2006.01)
*C07D 403/12* (2006.01)

(52) U.S. Cl. .................. 514/275; 544/323; 544/324; 544/325

(58) Field of Classification Search .............. 544/323, 544/324, 325; 514/275
See application file for complete search history.

(56) References Cited

U.S. PATENT DOCUMENTS

| | | |
|---|---|---|
| 4,018,913 A | 4/1977 | Okamoto et al. |
| 4,018,915 A | 4/1977 | Okamoto et al. |
| 4,036,955 A | 7/1977 | Okamoto et al. |
| 4,041,156 A | 8/1977 | Okamoto et al. |
| 4,046,876 A | 9/1977 | Okamoto et al. |
| 4,055,636 A | 10/1977 | Okamoto et al. |
| 4,055,651 A | 10/1977 | Okamoto et al. |
| 4,070,457 A | 1/1978 | Okamoto et al. |
| 4,073,914 A | 2/1978 | Kikumoto et al. |
| 4,085,057 A | 4/1978 | Masuda et al. |
| 4,096,255 A | 6/1978 | Kikumoto et al. |
| 4,104,392 A | 8/1978 | Okamoto et al. |
| 4,235,871 A | 11/1980 | Papahadjopoulos et al. |
| 4,438,122 A | 3/1984 | Holmwood et al. |
| 4,501,728 A | 2/1985 | Geho et al. |
| 4,505,910 A | 3/1985 | Bagli |
| 4,518,600 A | 5/1985 | Holmwood et al. |
| 4,544,402 A | 10/1985 | Schnurbusch et al. |
| 4,559,345 A | 12/1985 | Gomarasca et al. |
| 4,672,065 A | 6/1987 | Spatz |
| 4,837,028 A | 6/1989 | Allen et al. |
| 4,908,368 A | 3/1990 | Murase et al. |
| 4,959,364 A | 9/1990 | Mueller et al. |
| 4,992,439 A | 2/1991 | Meanwell |
| 5,011,472 A | 4/1991 | Aebischer et al. |
| 5,023,252 A | 6/1991 | Hseih et al. |
| 5,030,644 A | 7/1991 | Baldwin et al. |
| 5,120,734 A | 6/1992 | Klausener et al. |
| 5,238,934 A | 8/1993 | Knuppel et al. |
| 5,278,184 A | 1/1994 | Artico et al. |
| 5,510,332 A | 4/1996 | Kogan et al. |
| 5,580,868 A | 12/1996 | Lunkenheimer et al. |
| 5,770,573 A | 6/1998 | Arrhenius et al. |
| 5,814,643 A | 9/1998 | Duggan et al. |
| 5,861,429 A | 1/1999 | Sato et al. |
| 5,925,644 A | 7/1999 | Jakobi et al. |
| 5,942,504 A | 8/1999 | Grobelny |
| 5,955,491 A | 9/1999 | Sohda et al. |
| 5,962,479 A | 10/1999 | Chen |
| 5,972,946 A | 10/1999 | Murata et al. |
| 6,005,117 A | 12/1999 | Wehner et al. |

(Continued)

FOREIGN PATENT DOCUMENTS

CA 2241149 7/1997

(Continued)

OTHER PUBLICATIONS

Wolft Manfred E. "Burger's Medicinal Chemistry, 5ed, Part 1", John Wiley & Sons, 1995, pp. 975-977.*

(Continued)

*Primary Examiner*—Venkataraman Balasubramanian
(74) *Attorney, Agent, or Firm*—Swiss Tanner, P.C.

(57) ABSTRACT

Disclosed are compounds, which bind VLA-4. Certain of these compounds also inhibit leukocyte adhesion and, in particular, leukocyte adhesion mediated by VLA-4. Such compounds are useful in the treatment of inflammatory diseases in a human or animal subject such as asthma, Alzheimer's disease, atherosclerosis, AIDS dementia, diabetes, inflammatory bowel disease, Crohn's disease, rheumatoid arthritis, tissue transplantation, tumor metastasis and myocardial ischemia. The compounds can also be administered for the treatment of inflammatory brain diseases such as multiple sclerosis.

24 Claims, No Drawings

U.S. PATENT DOCUMENTS

| | | | |
|---|---|---|---|
| 6,436,904 B1 | 8/2002 | Ashwell et al. | |
| 6,479,492 B1 | 11/2002 | Konradi et al. | |
| 6,492,372 B1 | 12/2002 | Konradi et al. | |
| 6,544,994 B2 | 4/2003 | Rabelink et al. | |
| 6,545,003 B1 | 4/2003 | Grant et al. | |
| 6,689,781 B2 | 2/2004 | Konradi et al. | |
| 6,794,506 B2 | 9/2004 | Konradi et al. | |
| 6,903,088 B2 | 6/2005 | Konradi et al. | |
| 6,911,439 B2 | 6/2005 | Konradi et al. | |
| 7,005,433 B2 | 2/2006 | Konradi et al. | |
| 7,008,949 B2 | 3/2006 | Konradi et al. | |
| 7,026,328 B2 | 4/2006 | Konradi et al. | |
| 7,049,306 B2 | 5/2006 | Konradi et al. | |
| 7,135,477 B2 | 11/2006 | Konradi et al. | |
| 7,335,663 B2 | 2/2008 | Konradi et al. | |
| 7,378,529 B2 | 5/2008 | Konradi et al. | |
| 7,427,628 B2 | 9/2008 | Konradi et al. | |
| 7,452,912 B2 | 11/2008 | Grant et al. | |
| 7,579,466 B2 * | 8/2009 | Smith et al. | 544/323 |
| 2005/0203093 A1 | 9/2005 | Konradi et al. | |
| 2005/0261293 A1 | 11/2005 | Konradi et al. | |
| 2006/0013799 A1 | 1/2006 | Konradi et al. | |
| 2007/0099921 A1 | 5/2007 | Konradi et al. | |
| 2007/0129390 A1 | 6/2007 | Semko et al. | |
| 2007/0142416 A1 | 6/2007 | Semko et al. | |
| 2008/0058357 A1 | 3/2008 | Smith et al. | |

FOREIGN PATENT DOCUMENTS

| | | |
|---|---|---|
| CA | 2259224 | 1/1998 |
| CA | 2359115 | 7/2000 |
| DE | 195 36 891 | 4/1997 |
| DE | 265 56 36 | 6/1997 |
| DE | 195 48 709 A | 7/1997 |
| DE | 196 54 483 A | 1/1998 |
| DE | 197 13 000 | 10/1998 |
| EP | 116494 | 8/1984 |
| EP | 0 147 211 | 7/1985 |
| EP | 0 288 176 | 10/1988 |
| EP | 0 330 506 A2 | 8/1989 |
| EP | 0 330 506 A3 | 8/1989 |
| EP | 0 526 348 | 2/1993 |
| EP | 0 535 521 | 4/1993 |
| GB | 1500063 | 2/1978 |
| HU | 169926 | 2/1977 |
| JP | 59212480 | 12/1984 |
| WO | WO 91/05038 | 4/1991 |
| WO | WO 92/16549 | 10/1992 |
| WO | WO 93/12809 | 7/1993 |
| WO | WO 93/24154 | 12/1993 |
| WO | WO 96/01644 | 1/1996 |
| WO | WO 96/22966 | 8/1996 |
| WO | WO 96/32383 | 10/1996 |
| WO | WO 97/23451 | 7/1997 |
| WO | WO 97/48726 | 12/1997 |
| WO | WO 98/00395 | 1/1998 |
| WO | WO 98/22430 | 5/1998 |
| WO | WO 98/33783 | 8/1998 |
| WO | WO 98/53814 | 12/1998 |
| WO | WO 98/53817 | 12/1998 |
| WO | WO 99/06390 | 2/1999 |
| WO | WO 99/06391 | 2/1999 |
| WO | WO 99/06431 | 2/1999 |
| WO | WO 99/06432 | 2/1999 |
| WO | WO 99/06433 | 2/1999 |
| WO | WO 99/10312 | 3/1999 |
| WO | WO 99/10313 | 3/1999 |
| WO | WO 99/37605 | 7/1999 |
| WO | WO 99/37618 | 7/1999 |
| WO | WO 99/52898 | 10/1999 |
| WO | WO 00/18759 | 4/2000 |
| WO | WO 00/31067 | 6/2000 |
| WO | WO 00/43369 | 7/2000 |
| WO | WO 00/43371 | 7/2000 |
| WO | WO 00/43372 | 7/2000 |
| WO | WO 02/08201 | 1/2002 |
| WO | WO 03/099231 | 12/2003 |
| WO | WO 03/099809 | 12/2003 |
| WO | WO 2005/111020 | 11/2005 |
| WO | WO 2007/041270 | 4/2007 |
| WO | WO 2007/041324 | 4/2007 |
| WO | WO 2007/101165 | 9/2007 |

OTHER PUBLICATIONS

Banker, G.S. et al., "Modern Pharmaceutics, 3ed.", Marcel Dekker, New York. 1996, pp. 451 and 596.*

Tarkowski et al. Int. Arch. Allergy Immunol.121(1) 25-33, 2000.*

Grayson et al., J. Exp. Med., 188(11), 2187-2191, 1998.*

Tilley et al., Drugs of the Future, 26(10), 985-998, 2001.*

U.S. Appl. No. 12/645,154, filed Dec. 22, 2009, Konradi et al.

U.S. Appl. No. 12/637,719, filed Dec. 14, 2009, Konradi et al.

U.S. Appl. No. 12/579,828, filed Oct. 15, 2009, Semko et al.

Abraham, W.M., et al. "α4-Integrins Mediate Antigen-induced Late Bronchial Responses and Prolonged Airway Hyperresponsiveness in Sheep." *J. Clin. Invest.* 93: 776-787 (1994).

Abraham, et al., "Blockade of Late-phase Airway Responses and Airway Hyperresponsiveness in allergic Sheep with a Small-molecule Peptide Inhibitor of VLA-4," *Am J Resper Crit Care Med* 156:696-703 (1997).

Advani, S.B., et al. "Potential Antineoplastic Agents: N-(2-Benzoxazolyl)amino Acid Esters." *J. of Pharm. Sci.* 57(10): 1693-1696 (1968).

Anderson, et al., "Acute kidney graft rejection," *APMIS* 102, 23-37 (1994).

Anderson, et al., "Process Development of 5-Fluoro-3-[3-[4-(5-methoxy-4 pyrimidinyl)-1 piperazinyl]propyl]-1H-indole Dihydrochloride," *Org Proc Res Devel* 1:300-310 (1997).

Balaban, I., "An Investigation into the Formation of 4(5)-Aminoglyoxalines," *J. chem.. soc.* Part 1:1-268-273 (1930).

Bao, L., et al. "Correlation of VLA-4 integrin expression with metastatic potential in various human tumour cell lines." *Diff.* 52: 239-246 (1993).

Banker, G.S. et al., "Modern Pharmaceutics, 3ed.", Marcel Dekker, New York, pp. 451-596 (1996).

Baron, J.L., et al. "Surface Expression of α4 Integrin by CD4 T Cells is Required for Their Entry into Brain Parenchyma." *J. Exp. Med.* 177:57-68 (1993).

Baron, J.L., et al. "The Pathogenesis of Adeoptive Murine Autonimmune Diabetes Requires an Interaction between α4-Integrins and Vascular Cell Adhesion Molecule-1." *J. Clin. Invest.* 93: 1700-1708 (1994).

Belka et al., "Radiation induced CNS toxicity—Molecular and cellular mechanism" *Br. J. Cancer* 85:1233-1239 (2001).

Burkly, L.C., et al. "Protection Against Adoptive Transfer of Autoimmune Diabetes Mediated Through Very Late Antigent-4 Integrin." *Diabetes.* 43: 529-534 (1994).

Casanova et al., PubMed Abstract (*Rev Neurol.*) 28(9):909-915 (1999).

Chapman et al. "Time course of allergen-induced leukocyte accumulation in actively sensitized brown Norway rats" Am. J. Resp. Crit. Care Med. 153-154, A219 (1996).

Chapman et al. "Allergen-induced airway hyperreactivity and eosinophil accumulation are temporarily dissociated in actively sensitized brown Norway rats" Am. J. Resp. Crit. Care Med. 154-155, A881 (1997).

Chang et al. "Mechanism underlying the suppression of adjuvant-induced arthritis by 6-mercaptopurine" *Arth. Rheum.* 20; 1135-1141 (1997).

Chen, et al., "Mediation of sperm-egg fusion: evidence that mouse egg $\alpha^6\beta^1$ integrin is the receptor for sperm fertilinβ," *chem. Biol* 6:1-10 (1999).

Coito, et al., "Blockade of Very Late Antigen-4 Integrin Binding to fibronectin in Allograft Recipients," *Transplantation* 65:699-706 (1998).

Cybulsky, M.I., et al. "Endothelial Expression of a Mononuclear Leukocyte Adhesion Molecule During Atherogenesis."*Science.* 251: 788-791 (1991).

Damasio, et al., "Alzheimer's Disease and Related Dementias," *Cecil Textbook of Medicine*, $20^{th}$ Ed., vol. 2, pp. 1992-1996 (1996).

Elices, M.J., et al. "Expression and Functional Significance of Alternatively Spliced CS1 Fibronecting in Rheumatoid Arthritis Microvasculature." *J. Clin. Invest*. 93: 405-416 (1994).

Elices, M.J., et al. "VCAM-1 on Activated Endothelium Interacts with the Leukocyte Integrin VLA-4 at a Site Distinct from the CLA-4/Fibronectin Binding Site." *Cell*. 60: 577-584 (1990).

Elewaut, et al., "Distinctive Activated Cellular Subsets in Colon fronm Patients with Crohn's Disease and Ulcerative Colitis," *Scand. J. Gastroenterol* 33:743-748 (1998).

Ewenson, et al., "Analogues of substance P containing an $\alpha$-hydroxy, $\beta$-amino acid: synthesis and biological activity," *Eur J Med Chem* 26 435-442 (1991).

Freedman, et al, "Adhesion of Follicular Lymphoma Cells to Lymphoid germinal Centers—A Potential Mechanism of Tumor CellHoming Following Autologous Transplantation," *Leuk and Lymphome* 13:47 (1994).

Georczynski, et al., "Manipulation of skin graft rejection in alloimmune mice by anti-VCAM-1:VLA-4 but not anti-ICAM-1:LFA-1 monoclonal antibodies," *Trans Immunol* 3:55-61 (1995).

Georczynski, et al., "Altered patters of migration of cytokine-producing T lymphocytes in skin-grafted naïve or immune mice following in vivo administration of anti-VCAM-1 or ICAM-1", *Immunology* 87:573-580 (1996).

Giardina, et al., "Selective $\kappa$-Opioid Agonists: synthesis and Structure-ActivityFRelationships of Piperidines Incorporationg an Oxo-Containing Acyl Group,"*J. Med. Chem*. 37:3482-3491 (1994).

Gonzalez-Amaro et al., Therapeutic anti-integrin (alpha4 and alphaL) monoclonal antibodies: two-edged swords?, *Immunology*, vol. 116, No. 3, pp. 289-296, (2005).

Gordeev, M.F. "Combinatorial Approaches to pharmacophoric Heterocycles: A Solid-Phase Synthesis of 3,1-Benzoxazine-4-ones." *Biotech. and Bioengineering*. 61(1): 13-16 (1998).

Grayson, et al., $\alpha d\beta 2$ Integrin Is Expressed on Human Eosinophils and Functions as an Alternative Ligand for Vascular Cell Adhesion Molecule 1 (VCAM-1) *J. Exp. Med*. 188(11) 2187-2191 (1998).

Hamann., A., et al. "Role of $\alpha$4-Integrins in Lymphocute Homing to Mucosal Tissues in Vivo." *J. Immunology*. 152: 3283-3292 (1994).

Hartman, et. al., "Synthesis and Activity of Novel Nitropyrazines for use as Hypoxic Cell radiosensitizers," *J Med. Chem*. 27:1634-1639 (1984).

Henke, B.R., et al. "N-(2-Benzoylphenyl)-L-tyrosine :Aryl Agonists. 1. Discovery of a Novel Series of Potent Antihyperglycemic and Antihyperlipidemic Agents." *J. Med. Chem*. 41(25): 5020-5036 (1998).

Hladon, B., et al. In Vitro cytostatic activity of some amino acid 4-N-substituted cytosines. *Arch. Immunol. Ther. Exp*. 40(2): 145-150 (1992). (Abstract).

Hoffman, S., et al. "N-Pyrimidinylamino acids. III. N-(oxopyrimidinyl) derivatives of neutral amino acids." *Z. Chem*. 12(1): 21-22 (1972), CODEN: ZECEAL (Abstract).

Hoeve, et al., "Chiral Tetraalkylmethanes. Two Syntheses of Optically Active butylethylmethylpropylmethane of Known and High Optical Purity," *J. Org. Chem*. 45:2754-2763 (1980).

Hopewell et al. "Models of CNS radiation damage during space flight" Adv. Space Res. 14:433-442 (1994).

Jaeger, et al., "Peptidsynthesen mit-*O*-Carbamoyl-tyrosin Derivaten," *Chem. Ber*. 101:2762-2770 (1968) (English abstract), Only Abstract Considered.

Kawaguchi, S., et al. "VLA-4 Molecules on Tumor Cells Initiates an Adhesive Interaction with VCAM-1 Molecules on Endothelial Cell Surface."*Japanese J. Cancer Res*. 83: 1304-1316 (1992).

Kascheres et al., Chemical Abstract, DN 85:177351, also cited as *J. Org. Chem*. 41/22, 3546-9 (1976).

Keszthelyi, et al., "Evidence for a prolonged role of $\alpha_4$integrin throughout active experimental allergic encephalomyelitis," *Neurology* 47:1053-1059 (1996).

Korom, et al., "Blockade of Very late Angigen-4 Integrin Binding to Fibronectin in Allograft Recipients," *Transplantation* 65:854:859 (1998).

Kroneld, et al., "Expression of the Mucosal Lymphocyte Integrin $\alpha E\beta_7$ and its Ligand E-cadherin in Salivary Glands of Patients with Sjögren's Syndrome," *Scan. J. Rheumatol* 27:215-218 (1998).

Kung et al. "Involvement of IL-5 in a murine model of allergic pulmonary inflammation: prophylactic and therapeutic effect of an anti-IL-5 antibody" *Am J. Respir. Cell. Mol. Biol*. 13:360-365 (1995).

Lauri, D., et al. "Decreased adhesion to endothelial cells and matrix proteins of H-2K$^b$ gene transfected tumour cells." *British J. Cancer*. 68: 862-867 (1993).

Lazer, E.S., et al. "Benzoxazolamines and Benzothiazolamines: Potent, Enantioselective Inhibitors of Leukotriene Biosynthesis with a Novel Mechanism of Action." *J. Med. Chem*. 37(7): 913-923 (1994).

Li, H., et al. "An Atherogenic Diet Rapidly Induces VCAM-1, a Cytokine-Regulatable Mononuclear Leeukocyte Adhesion Molecule, in Rabbit Aortic Endothelium." *Arterioscler. Thromb*. 13(2): 197-204 (1993).

Luque, et al., "Activated Conformations of Very Late Activation Integrins Detected by a Group of Antibodies (HUTS) Specific for a Novel Regulatory Region (355-425) of the Common $\beta 1$ Chain", *J. Biol. Chem*. 271(19) 11067-11075 (1966).

Ma, D., et al. "Accelerating Effect Induced by the Structure of a-Amino Acid in the Copper Catalyzed Coupling Reaction of Aryl Halides with a-Amino Acids. Synthesis of Benzolactam-V8." *J. Am. Chem. Soc*.120(48): 12459-12467 (1998).

Marr-Leisy, et al., Chem. Abstract 105:97885, "The comparative spreading behavior of enantiomeric and racemic tyrosine amphiphiles," *Colloid & Polumer Sci*. 263:791-798 (1985).

Miller, S.D., et al., "Colloquium C15: Comparison of the ability of anti-VLA-4 antibody and a small molecule VLA-4 antagonist to regulate ongoing relapsing EAE," *Journal of Neurochemistry*, C15-02, 85:(Suppl. 1) (2003).

Miller, D.H., "Colloquium C15: Natalizumab (anti0VLA4 antibody) in multiple sclerosis," *Journal of Neurochemistry*, C15-04, 85: (Suppl. 1) (2003).

Mulligan, M.S., et al. "Role of $\beta 1$, $\beta 2$ Integrins and ICAM-1 in Lung Injury after Deposition of IgG and gA Immune Complexes." *J. Immunol*. 150(6): 2407-2417 (1993).

Ohta et al., "Emeheterone: Synthesis and Structural Revision," *Heterocycles* 31(9) 1655-1662 (1990).

Ohta et al., "Conversion of 2,5-Diphenyl- and 2,5-Dibenzylpyrazines to 2,5-Diketopiperazines", *Chem. Pharm. Bull* 27(12):2980-2987 (1979).

Okarhara, H., et al. "Involvement of Very Late Activation Antigen 4 (VLA-4) and Vascular Cell Adhesion Molecule 1(VCAM-1) in Tumor Necrosis Factor $\beta$ Enhancement of Experimental Metastasis." *Can. Res*. 54: 3233-3236 (1994).

Orosz et al., "Promotion of Experimental Liver Metastasis by Tumor Necrosis Factor," *Int. J. Cancer* 60:867-871 (1995).

Osborne, L. "Leukocyte Adhesion to Endothelium in Inflammation." *Cell*. 62: 3-6 (1990).

Paavonen, T., et al. "In Vivo Evidence of the Role of $\beta_4\beta_1$-VCAM-1 Interaction in Sarcoma, but not in Carcinoma Extravasation." *Int. J. Can*. 58: 298 (1994).

Palmer, et al., "Sequence and tissue Distribution of the Integrin $\alpha 9$ subnit, a Novel Partner of $\beta 1$ That Is Widely distributed in Epithelia and Muscle, "*J. Cell boil*. 123(5) 1289-1297 (1993).

Pang et al., "Up-Regulation of $\alpha E\beta 7$, A Novel Integrin Adhesion Molecule, on T Cells from Systemic Lupis Erythematosus Patients with Specific Epithelial Involvement," *Arthritis & Reumatism* 41(8):1456-1463 (1998).

Papaioannou, et al., Facile Preparation of the 1-Hydorxybenzotriazolyl Ester of N-Tritypyroglutamic Acid and its Application to the Synthesis of TRH, [D-His$^2$ ]TRH and Analogues Incorporation *cis*- and *rans*-Hydroxy-Lproline: *Acta Chemica Scand*. 49:103-114 (1995).

Paul, L.C., et al. "Monoclonal Antibodies Against LFA-1 and VLA-4 Inhibit Graft Vasculitis in Rat Cardiac Allografts." *Transpl. Proceed.* 25(1): 813-814 (1993).

Paul, et al., "Anti-integrin (LFA,-1, VLA-4, and Mac-1) antibody treatment and acutre cardiac graft rejection in the rat," *Transpl. Int.* 9:420-425 (1996).

Piraino, P.S. et al., "Prolonged reversal of chronic experimental allergic encephalomyelitis using a Small molecule inhibitor of a4 integrin," *Journal of Neuroimmunology*, 131:147-159 (2002).

Postigo, A.A., et al. "Increased Binding of Synovial T Lumphocytes from Rheumatoid Arthritis to Endothelial-Leukocyte Adhesion Molecule-1 (ELAM-1) and Vascular Cell Adhesion Molecule-1 (VCAM-1)." *J. Clin. Invest.* 89: 1445-1452 (1991).

Pretolani, M., et al. "Antibody to Very Late Activation Antigen 4 Prevents Antigen-induced Bronchial Hyperreactivity and Cellular Infiltration in the Guinea Pig Airways." *J. Exp. Med.* 180: 795-805 (1994).

Prusiner, S.B. "Novel proteinaceous infections particles cause scrapie" Science 216:136-144 (1982).

PubMed Abstract 12783578, also cited as *Expert Opinion Ther. Targets*, 7/3, 427-40 (2003).

PubMed Abstract 1287626, also cited as *Mol. Cell Neurosci.*, 23/3, 427-39 (2003).

PubMed Abstract 12877819, also cited as *Pulm. Pharmacol., Ther.*, 16/5, 279-85 (2003).

PubMed Abstract 12876405, also cited as *Int. Arch. Allergy Immunol.*, 31/3, 153-63 (2003).

Sandborn, et al, "Biologic Therapy of Inflammatory Bowel Disease," *Gastroenterology*, 122:1592-1608 (2002).

Sasseville, V.G., et al. "Monocyte Adhesion to Endothelium in Simian Immunodeficiency Virus-Induced AIDS Encephalitis is Mediated by Vascular Cell Adhesion Molecule-1/$\alpha_4\beta_1$ Integrin Interactions." *Am. J. Path.* 144(1): 27-40 (1994).

Schadendorf, D., et al. "Tumour Progression and Metastatic Behaviour In Vivo Correlates with Integrin Expression on Melanocytic Tumours." *J. Path.* 170: 429-434 (1993).

Schlegel, et al., "Inhibition of T Cell Costimulation by VCAM-1 revents Murine Graft-Versus-Host Disease Across Minor Histocompatibility Barriers,"*J. Immunol.* 155:3856-3865 (1995).

Schneider et al., "The role of α4 (CD49d) and β2 (CD18) integrins in eosinophil and neutrophil migration to allergic lung inflammation in the brown Norway rat" *Am. J. Respir. Cell. Mol. Biol.* 20:448-457 (1999).

Simchowitz, et al., "Polyvalent Cations Inhibit Human Neutrophil Chemotaxis by Interfering with the Ploymerization of Actin," *J. Biol. Chem.* 265(23)13457-13463 (1990).

Sonnenberg, A., "Integrins and Their Ligands," *Current Topics in Microbiology and Immunology* 184:7-35 (1993).

Springer, T.A. "Adhesion receptors of the immune system." *Nature.* 346: 425-434 (1990).

Springer, T.A., "Traffic Signals for Lymphocyte Recirculation and Leukocyte Emigration: The Multistep Paradigm," *Cell* 76:301-314 (1994).

Steinbach et al., "Expression of cell adhesion molecules in an established and characterized new human renal cancer cell line, CCF-RC7" *Urol. Res.* 23:175-183 (1995).

Tarkowski et al., PubMed Abstract (*Int Arch Allergy Immunol.*) 121(1):25-33 (2000).

Teranishi, K., et al. "Synthesis and Chemiluminescence of Coelenterazine (*Oplophorus* Luciferin) Analogues." *Bull. Chem. Soc. Jpn.* 63(11): 3132-3140 (1990).

Tilley et al., "VLA-4 antagonists," *Drugs of the Future*, 26(10):285-998 (2001).

Toniolo, et al., Chemical Abstract DN 77:5775, also cited as *J. Chem. Soc.*, Pekin Transactions, 1, Org. & Bio—org. Chem., 9/10, 1178-81 (1972).

Trollmo et al. "Expression of the mucosal lymphocyte integrin $\alpha^E\beta7$ and its ligand E-cadherin in the synovium of patients with rheumatoid arthritis" Scand. J. Immunol. 44:293-298 (1996).

Van Dinther-Janssen, A.C.H.M., et al. "Role of the CS1 adhesion motif of fibronectin in T cell adhesion to synovial membrane and peripheral lymph node endothelium." *Annals. Rheumatic Dis.* 52: 672-676 (1993).

Van Dinther-Janssen, A.C.H.M., et al. "The VLA-4/VCAM-1 Pathway is Involved in Lymphocyte Adhesion to Endothelium in Rheumatoid Synovium." *J. Immunology.* 147(12): 4207-4210 (1991).

Vedder, N.B., et al. "Role of neutrophils in generalized reperfusion injury associated with resuscitation from shock." *Surgery.* 106: 509-516 (1989).

Verhoef, et al., "Transport of peptide and protein drugs across biological membranes,"*Eur. J. Drug Metab. Pharmacokietics* 15(2):83-93 (1990).

Wen, et al., "The Chemistry of 1,2,3-Thiadiazoles. II. 3,4-Disubstituted Derivatives of 1,2,5-Thiadiazole 1,1-Dioxide," *J. Org. Chem.* 40(19):2743-2748 (1975).

Wen et al., "1,2,5-Thiadiazolid-3,4-Dione-1-Oxide", *Org. Prep. Proceed.* 1(4):255-258 (1969).

Whittaker, N., "A New Synthesis and the Chemical Properties of 5-Aminopyrimidine," *Chem.. Society* 354:1565-1570 (1951).

Wolft, M., "Burger's Medicinal Chemistry, 5ed, Part 1", John Wiley & Sons, (1995), pp. 975-977.

Wyzsza et al., Chemical Abstract DN 70:96568, also cited as Roczniki Chemii, 42/10, 1647-60 (1968) (English translation not provided).

Yamamoto et al. "Total synthesis of (±)-Celacinnine, (±)-celallocinnine, (±)-celafurine, (±)-celabenzine" *J. Am. Chem. Soc.* 103:6133-6136 (1981).

Yang, C-D., et al. "Inhibition of insultitis and prevention of diabetes in nonobese diabetic mice by blocking L-selecting and very late antigen 4 adhesion receptors." *Proc. Natl. Acad. Sci., USA.* 90: 10494-10498 (1993).

Yang, et al., "Prolongation of Rate Islet Allograft Survival by Treatment with Monoclonal Antibodies Against VLA-4 and LFA-1," *Transplantation* 60:71-76 (1995).

Yednock, T.A., et al. "Prevention of experimental autoimmune encephalomyelitis by antibodies against $\alpha_4\beta_1$ integrin."*Nature.* 356: 63 (1992).

Yednock, et al., "$\alpha_4\beta^1$ Inegrin-dependent Cell Adhesion Is Regulated by a Low Affinity Receptor Pool That is Conformationally Responsive to Ligand," *J. Biol. Chem.*, 270: 28740 (1965).

Yokosaki, et al., "The Integrinα9β1 Mediates Cell Attachment to a Non-RGD Site in the Third Fibronection Type III Repeat of Tenascin," *J. Biol. Chem.* 269:26691-26696 (1994).

Zhu, et al., "The Direct Formation of Funcationalized Alky(aryl)zinc Halides by Oxidative Addition of Highly Reactive Zinc with Organic Halides and Their Reactions with Acid Chlorides, αβ-Unsaturated Ketones, and Allylic, Aryl, and Vinyl Halides,"*J. Org. Chem.* 5:1445-1453 (1991).

Chem. Abstract 130:52724 structures for WO 9853814 dated Dec. 1998.

Chem. Abstract 69:676 structures for Jaeger et al., *Chem. Berichte* 101/8, 2762-70 (1968).

Chem. Abstract 105:97885 for structure, Marr-Leisy et al., *Coloid and Polymer Sc.* 263/10,79-8 (1985).

Chem Abstract 102:149279 for structure of JP 59212480 dated Dec. 1984.

Chem. Abstract 102:24642 for structures of EP 116494 dated Aug. 1984.

Chem. Abstract 125:89348 also cited as HCAPLUS, JP 08100141; Hiroshi et al., (1996).

Chem. Abstract 114:101454-1991:101454, also cited as Ohta et al., *Heterocycles*, 31/9, 166-62 (1990).

Chem. Abstract 113:130558-1990:530558, also cited as Simchowitz et al., *J. Biol. Chem.*, 265/23, 13457-63 (1990).

Chem. Abstract 93:46584-1980:446584, also cited as Ohta et al., *Chem. & Pharmaceutical Bulletin*, 27/12, 2980-7 (1979).

* cited by examiner

PYRIMIDINYL SULFONAMIDE COMPOUNDS WHICH INHIBIT LEUKOCYTE ADHESION MEDIATED BY VLA-4

CROSS-REFERENCE TO RELATED APPLICATIONS

This application is a Continuation Patent Application of U.S. Utility patent application Ser. No. 11/679,042 filed Feb. 26, 2007, now U.S. Pat. No. 7,579,466, which claims priority from U.S. Provisional Patent Application No. 60/777,595, filed on Feb. 27, 2006, the disclosure of which applications are all is incorporated herein by reference in its their entirety.

BACKGROUND OF THE INVENTION

Field of the Invention

This invention relates to compounds which inhibit leukocyte adhesion and, in particular, leukocyte adhesion mediated by α4 integrins, where the α4 integrin is preferably VLA-4. This invention also relates to pharmaceutical compositions comprising such compounds as well as methods for treating, e.g., inflammation, using either the compounds or the pharmaceutical compositions of this invention.

REFERENCES

The following publications are cited in this application as superscript numbers:

1 Hemler and Takada, European Patent Application Publication No. 330,506, published Aug. 30, 1989
2 Elices, et al., Cell, 60:577 584 (1990)
3 Springer, Nature, 346:425 434 (1990)
4 Osborn, Cell, 62:3 6 (1990)
5 Vedder, et al., Surgery, 106:509 (1989)
6 Pretolani, et al., J. Exp. Med., 180:795 (1994)
7 Abraham, et al., J. Clin. Invest., 93:776 (1994)
8 Mulligan, et al., J. Immunology, 150:2407 (1993)
9 Cybulsky, et al., Science, 251:788 (1991)
10 Li, et al., Arterioscler. Thromb., 13:197 (1993)
11 Sasseville, et al., Am. J. Path., 144:27 (1994)
12 Yang, et al., Proc. Nat. Acad. Science (USA), 90:10494 (1993)
13 Burkly, et al., Diabetes, 43:529 (1994)
14 Baron, et al., J. Clin. Invest., 93:1700 (1994)
15 Hamann, et al., J. Immunology, 152:3238 (1994)
16 Yednock, et al., Nature, 356:63 (1992)
17 Baron, et al., J. Exp. Med., 177:57 (1993)
18 van Dinther-Janssen, et al., J. Immunology, 147:4207 (1991)
19 van Dinther-Janssen, et al., Annals. Rheumatic Dis., 52:672 (1993)
20 Elices, et al., J. Clin. Invest., 93:405 (1994)
21 Postigo, et al., J. Clin. Invest., 89:1445 (1991)
22 Paul, et al., Transpl. Proceed., 25:813 (1993)
23 Okarhara, et al., Can. Res., 54:3233 (1994)
24 Paavonen, et al., Int. J. Can., 58:298 (1994)
25 Schadendorf, et al., J. Path., 170:429 (1993)
26 Bao, et al., Diff., 52:239 (1993)
27 Lauri, et al., British J. Cancer, 68:862 (1993)
28 Kawaguchi, et al., Japanese J. Cancer Res., 83:1304 (1992)
29 Konradi, et al., PCT/US00/01686, filed, Jan. 21, 2000

All of the above publications are herein incorporated by reference in their entirety to the same extent as if each individual publication was specifically and individually indicated to be incorporated by reference in its entirety.

STATE OF THE ART

VLA-4 (also referred to as α4β1 integrin and CD49d/CD29), first identified by Hemler and Takada,[1] is a member of the β1 integrin family of cell surface receptors, each of which comprises two subunits, an α chain and a β chain. VLA-4 contains an α4 chain and a β1 chain. There are at least nine β1 integrins, all sharing the same β1 chain and each having a distinct α chain. These nine receptors all bind a different complement of the various cell matrix molecules, such as fibronectin, laminin, and collagen. VLA-4, for example, binds to fibronectin. VLA-4 also binds non-matrix molecules that are expressed by endothelial and other cells. These non-matrix molecules include VCAM-1, which is expressed on cytokine-activated human umbilical vein endothelial cells in culture. Distinct epitopes of VLA-4 are responsible for the fibronectin and VCAM-1 binding activities and each activity has been shown to be inhibited independently.[2]

Intercellular adhesion mediated by VLA-4 and other cell surface receptors is associated with a number of inflammatory responses. At the site of an injury or other inflammatory stimulus, activated vascular endothelial cells express molecules that are adhesive for leukocytes. The mechanics of leukocyte adhesion to endothelial cells involves, in part, the recognition and binding of cell surface receptors on leukocytes to the corresponding cell surface molecules on endothelial cells. Once bound, the leukocytes migrate across the blood vessel wall to enter the injured site and release chemical mediators to combat infection. For reviews of adhesion receptors of the immune system, see, for example, Springer[3] and Osborn.[4]

Inflammatory brain disorders, such as experimental autoimmune encephalomyelitis (EAE), multiple sclerosis (MS) and meningitis, are examples of central nervous system disorders in which the endothelium/leukocyte adhesion mechanism results in destruction to otherwise healthy brain tissue. Large numbers of leukocytes migrate across the blood brain barrier (BBB) in subjects with these inflammatory diseases. The leukocytes release toxic mediators that cause extensive tissue damage resulting in impaired nerve conduction and paralysis.

In other organ systems, tissue damage also occurs via an adhesion mechanism resulting in migration or activation of leukocytes. For example, it has been shown that the initial insult following myocardial ischemia to heart tissue can be further complicated by leukocyte entry to the injured tissue causing still further insult (Vedder, et al.).[5] Other inflammatory or medical conditions mediated by an adhesion mechanism include, by way of example, asthma,[6-8] Alzheimer's disease, atherosclerosis,[9-10] AIDS dementia,[11] diabetes[12-14] (including acute juvenile onset diabetes), inflammatory bowel disease[15] (including ulcerative colitis and Crohn's disease), multiple sclerosis,[16-17] rheumatoid arthritis,[18-21] tissue transplantation,[22] tumor metastasis,[23-28] meningitis, encephalitis, stroke, and other cerebral traumas, nephritis, retinitis, atopic dermatitis, psoriasis, myocardial ischemia and acute leukocyte-mediated lung injury such as that which occurs in adult respiratory distress syndrome.

Substituted aminopyrimidines, as a class, have been disclosed as inhibiting binding of VLA-4 to VCAM-1 and, accordingly, exhibit anti-inflammatory properties.[29] While these compounds possess antagonist properties to such binding, enhanced bioavailability of these compounds would augment their efficacy.

SUMMARY OF THE INVENTION

This invention provides compounds, pharmaceutically acceptable salts and esters thereof, compositions thereof, syntheses thereof, and methods for treating VLA-4 mediated diseases. Based on in vivo data for those compounds of this invention, which were so evaluated, these compounds are contemplated to exhibit enhanced bioavailability when orally delivered as measured by conventional area under the curve (AUC) analysis.

In one embodiment, the present invention provides compounds of formula I:

[Structure I]

wherein:
$R^1$ is selected from the group consisting of $C_1$ to $C_4$ alkyl and $C_1$ to $C_4$ haloalkyl; and
$R^2$ is selected from the group consisting of $C_1$ to $C_4$ alkyl, $C_2$ to $C_4$ alkenyl, $C_2$ to $C_4$ alkynyl, and $C_3$-$C_6$ cycloalkyl;
or pharmaceutically acceptable salts, or esters thereof.

In some embodiments, $R^1$ is $C_1$ to $C_2$ alkyl. In other embodiments, $R^1$ is methyl or trifluoromethyl. In still other embodiments, $R^1$ is methyl.

In some embodiments, $R^2$ is $C_1$ to $C_4$ alkyl. In other embodiments, $R^2$ is $C_1$ to $C_3$ alkyl. In still other embodiments, $R^2$ is methyl, ethyl, isopropyl or n-propyl. In another embodiment $R^2$ is methyl or ethyl, and in yet another embodiment, $R^2$ is isopropyl.

In some embodiments, $R^2$ is $C_3$ to $C_6$ cycloalkyl. In other embodiments, $R^2$ is cyclopentyl.

In some embodiments, $R^2$ is $C_2$ to $C_4$ alkenyl. In other embodiments, $R^2$ is allyl.

In some embodiments, $R^2$ is $C_2$ to $C_4$ alkynyl. In other embodiments, $R^2$ is propargyl.

Examples of compounds of this invention include those having the $R^1$ and $R^2$ groups recited in Table 1 (including pharmaceutically acceptable salts, or esters thereof).

TABLE 1

[Structure]

| $R^1$ | $R^2$ |
| --- | --- |
| trifluoromethyl | ethyl |
| methyl | isopropyl |
| methyl | cyclopentyl |

TABLE 1-continued

[Structure]

| $R^1$ | $R^2$ |
| --- | --- |
| methyl | methyl |
| methyl | propargyl |
| methyl | ethyl |
| methyl | allyl |
| butyl | ethyl |
| 3-chloropropyl | ethyl |
| 3-chloropropyl | methyl |
| 3,3,3-trifluoropropyl | ethyl |
| propyl | ethyl |
| isopropyl | ethyl |

In another embodiment, the present invention provides a compound of formula II:

[Structure II]

wherein:
$R^1$ is selected from the group consisting of $C_1$ to $C_4$ alkyl and $C_1$ to $C_4$ haloalkyl; and
$R^2$ is selected from the group consisting of $C_1$ to $C_4$ alkyl, $C_2$ to $C_4$ alkenyl, $C_2$ to $C_4$ alkynyl, and $C_3$-$C_6$ cycloalkyl;
or pharmaceutically acceptable salts, or esters thereof.

In some embodiments, $R^1$ is $C_1$ to $C_2$ alkyl. In other embodiments, $R^1$ is methyl or trifluoromethyl. In still other embodiments, $R^1$ is methyl.

In some embodiments, $R^2$ is $C_1$ to $C_4$ alkyl. In other embodiments, $R^2$ is $C_1$ to $C_3$ alkyl. In still other embodiments, $R^2$ is methyl, ethyl, isopropyl or n-propyl. In another embodiment $R^2$ is methyl or ethyl, and in yet another embodiment, $R^2$ is isopropyl.

In some embodiments, $R^2$ is $C_3$ to $C_6$ cycloalkyl. In other embodiments, $R^2$ is cyclopentyl.

In some embodiments, $R^2$ is $C_2$ to $C_4$ alkenyl. In other embodiments, $R^2$ is allyl.

In some embodiments, $R^2$ is $C_2$ to $C_4$ alkynyl. In other embodiments, $R^2$ is propargyl.

Examples of compounds of this invention include those having the $R^1$ and $R^2$ groups recited in Table 2 (including pharmaceutically acceptable salts, or esters thereof).

TABLE 2

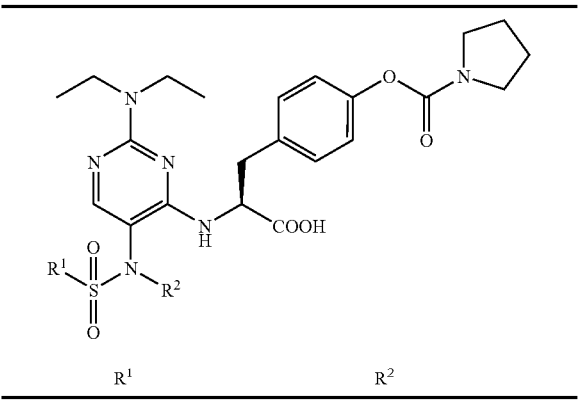

| R¹ | R² |
|---|---|
| trifluoromethyl | ethyl |
| methyl | isopropyl |
| methyl | cyclopentyl |
| methyl | methyl |
| methyl | propargyl |
| methyl | ethyl |
| methyl | allyl |
| butyl | ethyl |
| 3-chloropropyl | ethyl |
| 3-chloropropyl | methyl |
| 3,3,3-trifluoropropyl | ethyl |

TABLE 2-continued

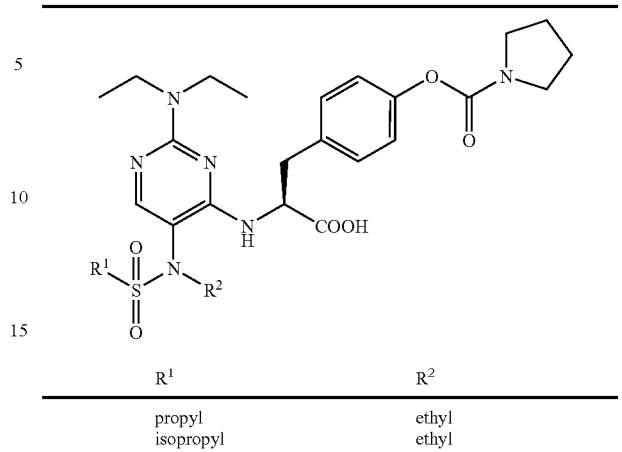

| R¹ | R² |
|---|---|
| propyl | ethyl |
| isopropyl | ethyl |

Ortho and meta substitution of the pyrrolidinylcarbonyloxy group on the phenyl ring are also within the scope of this invention.

This invention also provides for the compounds in Table 3 as well as their pharmaceutically acceptable salts, or esters thereof.

TABLE 3

| | Structure | Name |
|---|---|---|
| 3-1 | 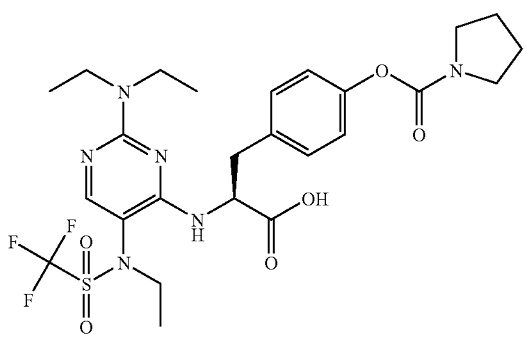 | (S)-2-(2-(diethylamino)-5-(N-ethyl-1,1,1-trifluoromethylsulfonamido)pyrimidin-4-ylamino)-3-(4-(pyrrolidine-1-carbonyloxy)phenyl)propanoic acid |
| 3-2 | 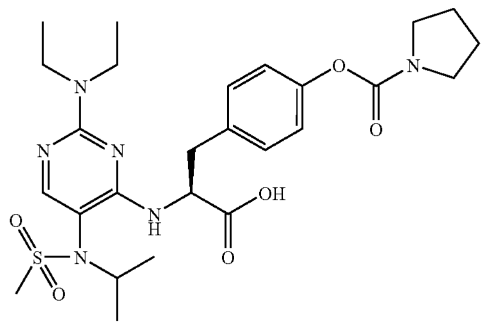 | (S)-2-(2-(diethylamino)-5-(N-isopropylmethylsulfonamido)pyrimidin-4-ylamino)-3-(4-(pyrrolidine-1-carbonyloxy)phenyl)propanoic acid |

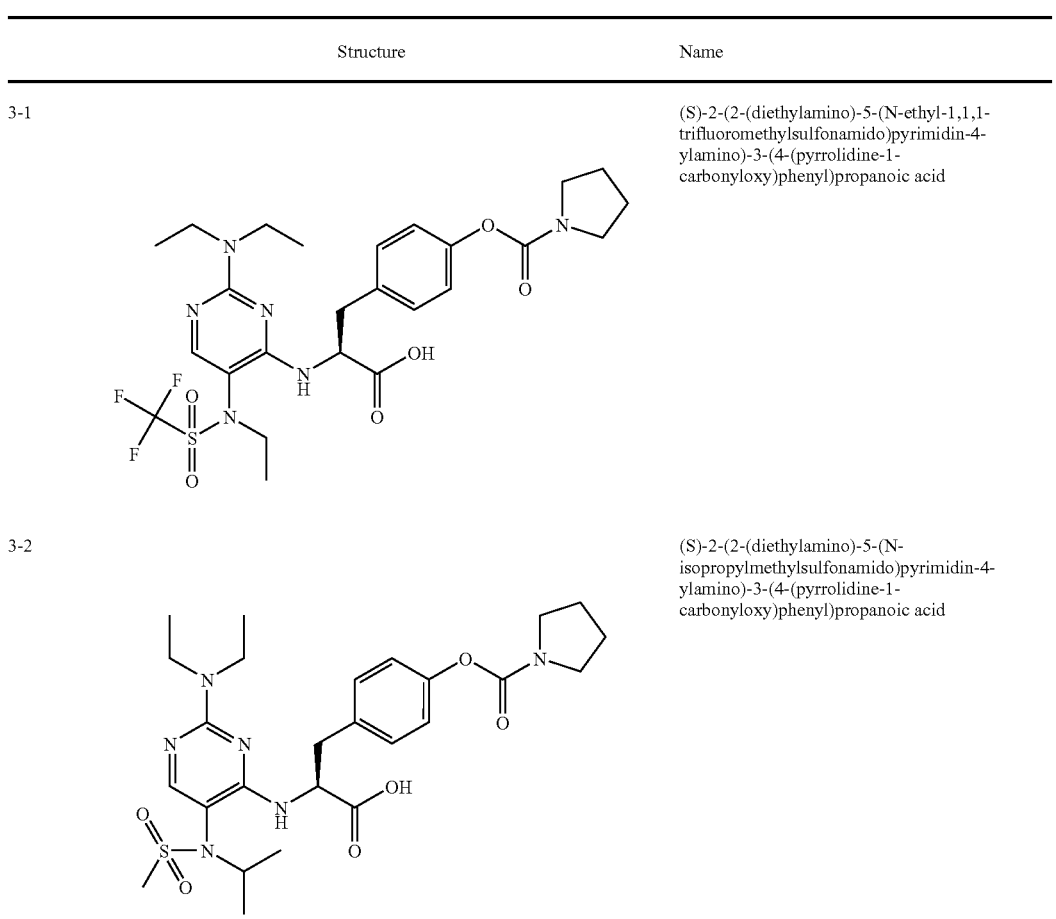

TABLE 3-continued

| | Structure | Name |
|---|---|---|
| 3-3 | 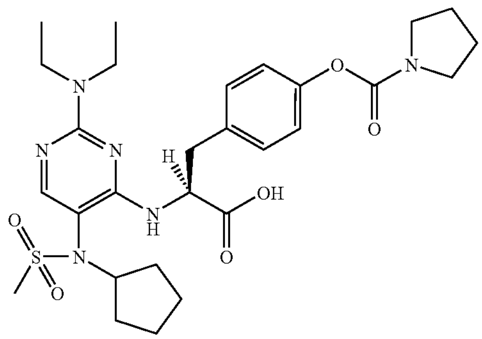 | (S)-2-(5-(N-cyclopentylmethylsulfonamido)-2-(diethylamino)pyrimidin-4-ylamino)-3-(4-(pyrrolidine-1-carbonyloxy)phenyl)propanoic acid |
| 3-4 | 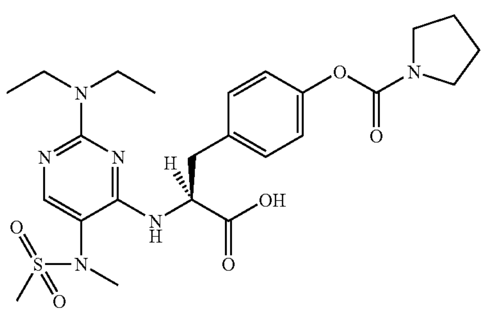 | (S)-2-(2-(diethlamino-5-(N-methylmethylsulfonamido)pyrimidin-4-ylamino)-3-(4-(pyrrolidine-1-carbonyloxy)phenyl)propanoic acid |
| 3-5 | 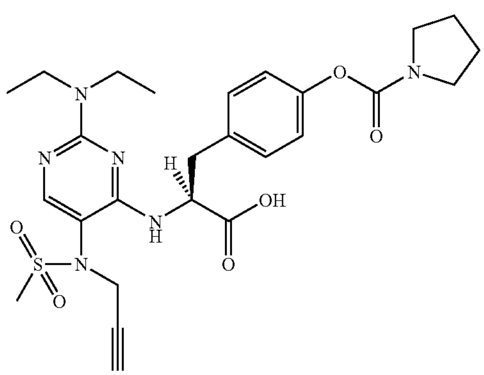 | (S)-2-(2-(diethylamino)-5-(N-(prop-2-ynyl)methylsulfonamido)pyrimidin-4-ylamino)-3-(4-(pyrrolidine-1-carbonyloxy)phenyl)-propanoic acid |
| 3-6 | 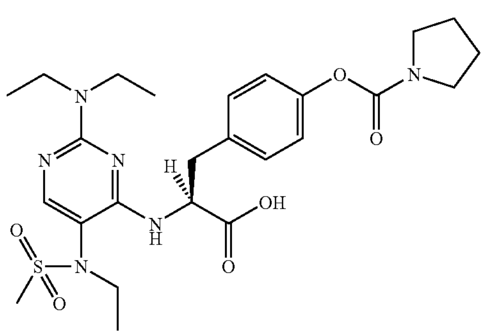 | (S)-2-(2-(diethylamino)-5-(N-ethylmethylsulfonamido)pyrimidin-4-ylamino)-3-(4-(pyrrolidine-1-carbonyloxy)phenyl)-propanoic acid |

TABLE 3-continued

| | Structure | Name |
|---|---|---|
| 3-7 | 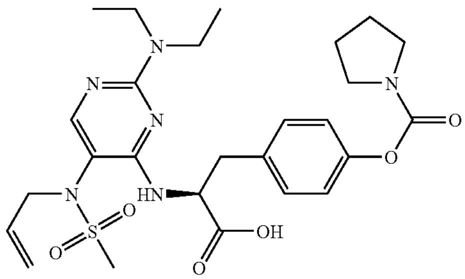 | (S)-2-(5-(N-allylmethylsulfonamido)-2-(diethylamino)pyrimidin-4-ylamino)-3-(4-(pyrrolidine-1-carbonyloxy)phenyl)propanoic acid |
| 3-8 | 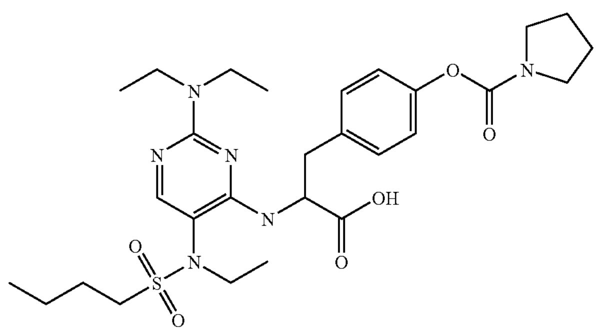 | (S)-2-(2-(diethylamino)-5-(N-ethylbutylsulfonamido)pyrimidin-4-ylamino)-3-(4-(pyrrolidine-1-carbonyloxy)phenyl)-propanoic acid |
| 3-9 | 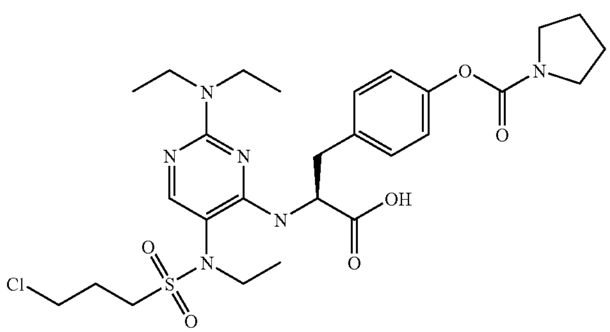 | (S)-2-(5-(3-Chloro-N-ethylpropylsulfonamido)-2-(diethylamino)-pyrimidin-4-ylamino)-3-(4-(pyrrolidine-1-carbonyloxy)phenyl)propanoic acid |
| 3-10 | 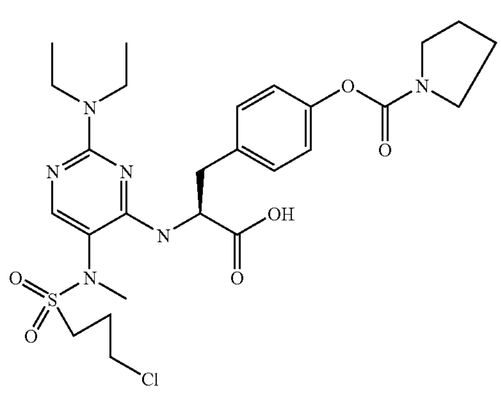 | (S)-2-(5-(3-chloro-N-methylpropyl-sulfonamido)-2-(diethylamino)pyrimidin-4-ylamino)-3-(4-(pyrrolidine-1-carbonyloxy)phenyl)propanoic acid |

TABLE 3-continued

| | Structure | Name |
|---|---|---|
| 3-11 | 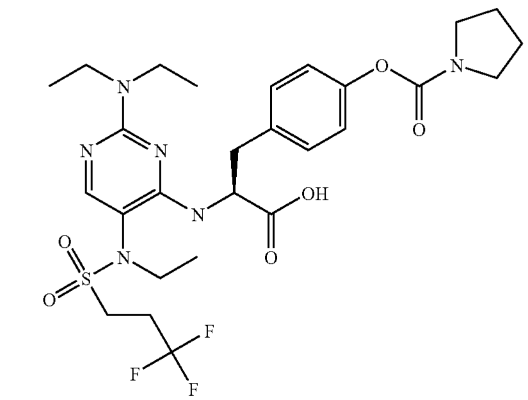 | (S)-2-(2-(diethylamino)-5-(N-ethyl-3,3,3-trifluoropropylsulfonamido)-pyrimidin-4-ylamino)-3-(4-(pyrrolidine-1-carbonyloxy)phenyl)propanoic acid |
| 3-12 | 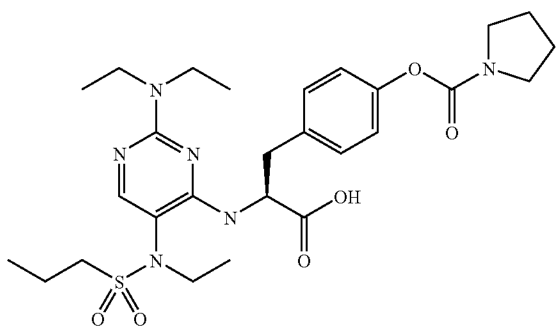 | (S)-2-(2-(diethylamino)-5-(N-ethylpropylsulfonamido)pyrimidin-4-ylamino)-3-(4-(pyrrolidine-1-carbonyloxy)phenyl)-propanoic acid |
| 3-13 | 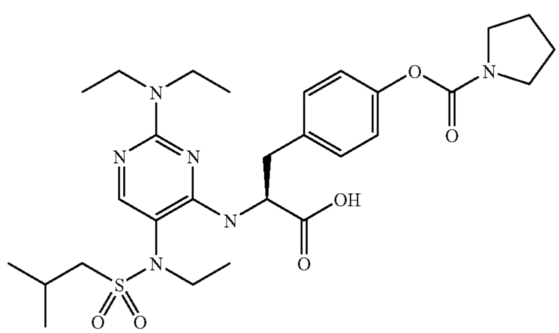 | (S)-2-(2-(diethylamino)-5-(N-ethyl-2-methylpropylsulfonamido)pyrimidin-4-ylamino)-3-(4-(pyrrolidine-1-carbonyloxy)-phenyl)propanoic acid |

In another aspect, this invention provides pharmaceutical compositions comprising a pharmaceutically acceptable carrier and a therapeutically effective amount of one or more of the compounds defined herein.

In one of its method aspects, this invention is directed to a method for treating a disease mediated at least in part by α4 integrin, preferably VLA-4, in a patient, which method comprises administering a pharmaceutical composition comprising a pharmaceutically acceptable carrier and a therapeutically effective amount of one or more of the compounds of this invention.

The compounds and pharmaceutical compositions of this invention are useful for treating disease conditions mediated at least in part by α4 integrins, where the α4 integrin is preferably VLA-4 or leucocyte adhesion. Such disease conditions include, by way of example, asthma, Alzheimer's disease, atherosclerosis, AIDS dementia, diabetes (including acute juvenile onset diabetes), inflammatory bowel disease (including ulcerative colitis and Crohn's disease), multiple sclerosis, rheumatoid arthritis, tissue transplantation, tumor metastasis, meningitis, encephalitis, stroke, and other cerebral traumas, nephritis, retinitis, atopic dermatitis, psoriasis, myocardial ischemia and acute leukocyte-mediated lung injury such as that which occurs in adult respiratory distress syndrome.

Other disease conditions include, but are not limited to, inflammatory conditions such as erythema nodosum, allergic conjunctivitis, optic neuritis, uveitis, allergic rhinitis, Ankylosing spondylitis, psoriatic arthritis, vasculitis, Reiter's syndrome, systemic lupus erythematosus, progressive systemic sclerosis, polymyositis, dermatomyositis, Wegner's granulomatosis, aortitis, sarcoidosis, lymphocytopenia, temporal arteritis, pericarditis, myocarditis, congestive heart failure, polyarteritis nodosa, hypersensitivity syndromes, allergy, hypereosinophilic syndromes, Churg-Strauss syndrome, chronic obstructive pulmonary disease, hypersensitivity pneumonitis, chronic active hepatitis, interstitial cystitis, autoimmune endocrine failure, primary biliary cirrhosis, autoimmune aplastic anemia, chronic persistent hepatitis and thyroiditis.

In one embodiment, the disease condition mediated by α4 integrin is an inflammatory disease.

In another embodiment, the disease condition is an autoimmune disease.

In some embodiments, the disease is selected from asthma, multiple sclerosis and inflammatory bowel disease. In other embodiments the disease is Crohn's disease. In yet other embodiments the disease is rheumatoid arthritis.

In another aspect, this invention provides a method for preparing a compound of formula I:

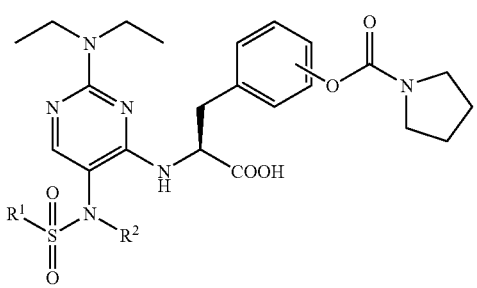

wherein:
$R^1$ is selected from the group consisting of $C_1$ to $C_4$ alkyl and $C_1$ to $C_4$ haloalkyl; and
$R^2$ is selected from the group consisting of $C_1$ to $C_4$ alkyl, $C_2$ to $C_4$ alkenyl, $C_2$ to $C_4$ alkynyl, and $C_3$-$C_6$ cycloalkyl;
or pharmaceutically acceptable salts, or esters thereof, which method comprises:
a) contacting a compound of formula III

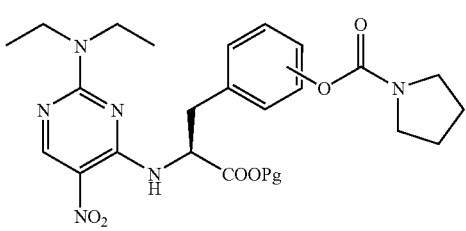

where Pg is a carboxyl protecting group;
with a $C_1$ to $C_4$ aldehyde or ketone, a $C_2$ to $C_4$ alkenyl aldehyde or ketone, $C_2$ to $C_4$ alkynyl aldehyde or ketone, $C_3$-$C_6$ cycloalkyl ketone and benzaldehyde under reductive amination conditions to provide for a compound of formula IV:

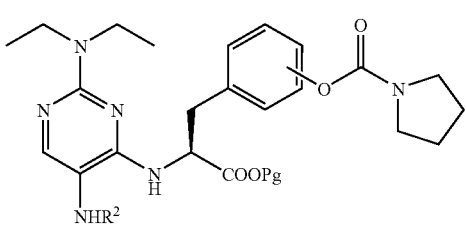

b) contacting compound IV with a sulfonyl halide of the formula $R^1SO_2Z$ where Z is halo under conditions to form a compound of formula V:

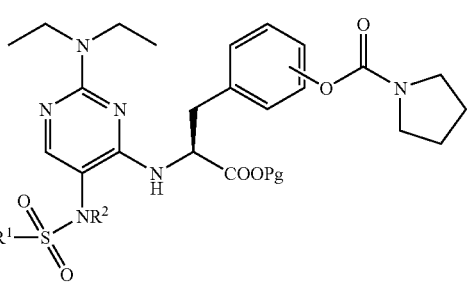

and
c) removing the carboxyl protecting group to provide for a compound of formula I.

In another aspect, this invention provides a method for preparing a compound of formula I

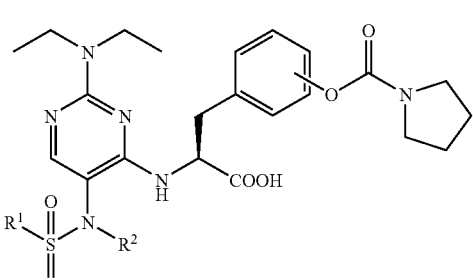

wherein:
$R^1$ is selected from the group consisting of $C_1$ to $C_4$ alkyl and $C_1$ to $C_4$ haloalkyl; and
$R^2$ is selected from the group consisting of $C_1$ to $C_4$ alkyl, $C_2$ to $C_4$ alkenyl, $C_2$ to $C_4$ alkynyl, and $C_3$-$C_6$ cycloalkyl;
or pharmaceutically acceptable salts, or esters, thereof, which method comprises:
a) contacting a compound of formula VI

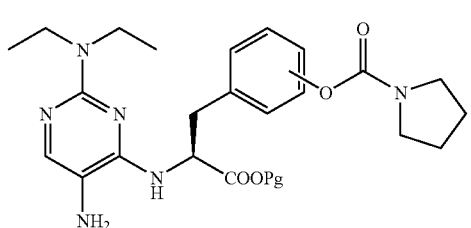

where Pg is a carboxyl protecting group;
with an excess of $R'SO_2X$ to provide for a compound of formula VII:

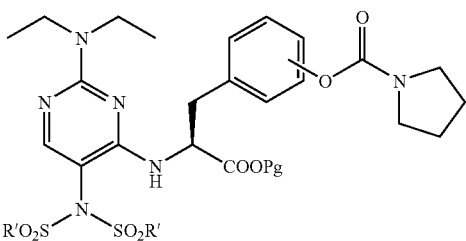

VII b) selectively removing a single —SO$_2$R' group from the compound of formula VII to provide a compound of formula VIII:

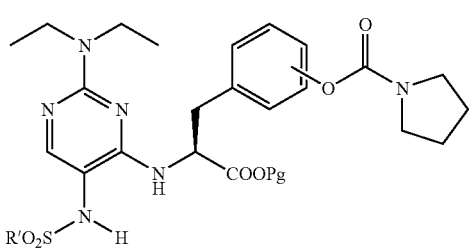

VIII c) contacting compound VIII with an alkylating agent with a formula R$^2$—X, wherein X is halo, or with dimethylsulfate when R$^2$ is methyl, to form a compound of formula IX:

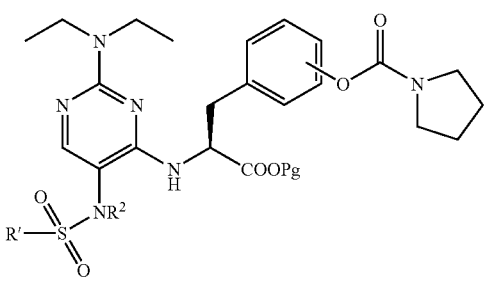

IX and d) removing the carboxyl protecting group to provide for a compound of formula I.

DETAILED DESCRIPTION OF THE INVENTION

As stated above, this invention relates to compounds which inhibit leukocyte adhesion and, in particular, leukocyte adhesion mediated at least in part by α4 integrins, preferably VLA-4. However, prior to describing this invention in further detail, the following terms will first be defined.

DEFINITIONS

Unless otherwise stated, the following terms used in the specification and claims have the meanings given below:

As used herein and unless otherwise defined, "alkyl" refers to monovalent straight and branched hydrocarbyl groups having from 1 to 4 carbon atoms and preferably 1 to 3 carbon atoms. This term is exemplified by groups such as methyl, ethyl, n-propyl, iso-propyl, n-butyl, iso-butyl, sec-butyl, and t-butyl.

"Alkenyl" refers to straight or branched monovalent hydrocarbyl groups from 2 to 4 carbon atoms and preferably 2 to 3 carbon atoms and having at least 1 and preferably 1 site of vinyl (>C=C<) unsaturation. Examples of such alkenyl groups include vinyl (—CH=CH$_2$), allyl (—CH$_2$CH=CH$_2$), n-propen-1-yl (—CH=CHCH$_3$), n-buten-2-yl (—CH$_2$CH=CHCH$_3$), and the like. Included within this term are the cis and trans isomers or mixtures of these isomers.

"Alkynyl" refers to straight or branched monovalent hydrocarbyl groups having from 2 to 4 carbon atoms and preferably 2 to 3 carbon atoms and having at least 1 and preferably 1 site of acetylenic —C≡C— unsaturation. Examples of such alkynyl groups include acetylenyl (—C≡CH), propargyl (—CH$_2$C≡CH), n-propyn-1-yl (—CH≡CHCH$_3$), and the like.

"Halo" or "halogen" refers to fluoro, chloro, bromo and iodo and preferably is either fluoro or chloro.

"Haloalkyl" refers to alkyl groups having from 1 to 5 halo groups. Preferably, such groups have from 1 to 3 halo groups and 1 to 2 carbon atoms. Exemplary haloalkyl groups include halomethyl (e.g., fluoromethyl), dihalomethyl (e.g., difluoromethyl), trihalomethyl (e.g., trifluoromethyl), haloethyl (e.g. 2-chloroeth-1-yl), trihaloethyl (e.g., 2,2,2-trifluoroeth-1-yl), halopropyl (e.g., 3-chloroprop-1-yl and trihalopropyl (e.g., 3,3,3-trifluoroprop-1-yl).

"Pharmaceutically acceptable carrier" means a carrier that is useful in preparing a pharmaceutical composition that is generally safe, non-toxic and neither biologically nor otherwise undesirable, and includes a carrier that is acceptable for veterinary use as well as human pharmaceutical use. "A pharmaceutically acceptable carrier" as used in the specification and claims includes both one and more than one such carrier.

"Pharmaceutically acceptable salt" refers to salts which retain the biological effectiveness and properties of the compounds of this invention and which are not biologically or otherwise undesirable. In many cases, the compounds of this invention are capable of forming acid and/or base salts by virtue of the presence of amino and/or carboxyl groups or groups similar thereto.

Pharmaceutically-acceptable base addition salts can be prepared from inorganic and organic bases. Salts derived from inorganic bases, include by way of example only, sodium, potassium, lithium, ammonium, calcium, and magnesium salts. Salts derived from organic bases include, but are not limited to, salts of primary, secondary, and tertiary amines, such as alkyl amines, dialkyl amines, trialkyl amines, substituted alkyl amines, di(substituted alkyl) amines, tri (substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and triamines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group.

Examples of suitable amines include, by way of example only, isopropylamine, trimethyl amine, diethyl amine, tri(isopropyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like. It should also be understood that other carboxylic acid derivatives would be useful in the practice of this invention, for example, carboxylic acid amides, including carboxamides, lower alkyl carboxamides, dialkyl carboxamides, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

The term "pharmaceutically-acceptable cation" refers to the cation of a pharmaceutically-acceptable salt.

It is understood that in all substituted groups defined herein, polymers arrived at by defining substituents with further substituents to themselves (e.g., substituted aryl having a substituted aryl group as a substituent which is itself substituted with a substituted aryl group, etc.) are not intended for inclusion herein. In such cases, the maximum number of such substituents is three. That is to say that each of the above definitions is constrained by a limitation that, for example, substituted aryl groups are limited to -substituted aryl-(substituted aryl)-(substituted aryl).

"Treating" or "treatment" of a disease includes:

(1) preventing the disease, i.e., causing the clinical symptoms of the disease not to develop in a mammal that may be exposed to or predisposed to the disease but does not yet experience or display symptoms of the disease, (2) inhibiting the disease, i.e., arresting or reducing the development of the disease or its clinical symptoms, or (3) relieving the disease, i.e., causing regression of the disease or its clinical symptoms.

A "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

Integrins are a large family of homologous transmembrane linker proteins that are the principal receptors on animal cells for binding most extracellular matrix proteins, such as collagen, fibronectin, and laminin. The integrins are heterodimers comprised of an $\alpha$ chain and a $\beta$ chain. To date, twenty different integrin heterodimers, made from 9 different $\alpha$ subunits and 14 different $\beta$ subunits, have been identified. The term "$\alpha 4$ integrins" refers to the class of heterodimer, enzyme-linked cell-surface receptors that contain the $\alpha 4$ subunit paired with any of the $\beta$ subunits. VLA-4 is an example of an $\alpha 4$ integrin, and is a heterodimer of the $\alpha 4$ and $\beta 1$ subunits, and is also referred to as $\alpha 4 \beta 1$ integrin.

Compound Preparation

The compounds of this invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts, *Protecting Groups in Organic Synthesis*, Second Edition, Wiley, New York, 1991, and references cited therein.

Furthermore, the compounds of this invention will typically contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included within the scope of this invention, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

Most compounds of this invention were named using ChemDraw v. 10.0, (available from Cambridgesoft at 100 Cambridge Park Drive, Cambridge, Mass. 02140).

In one embodiment, the compounds of this invention can be prepared as described below in Scheme 1 where for illustrative purposes only, $R^1$ is methyl and $R^2$ is isopropyl.

Scheme 1

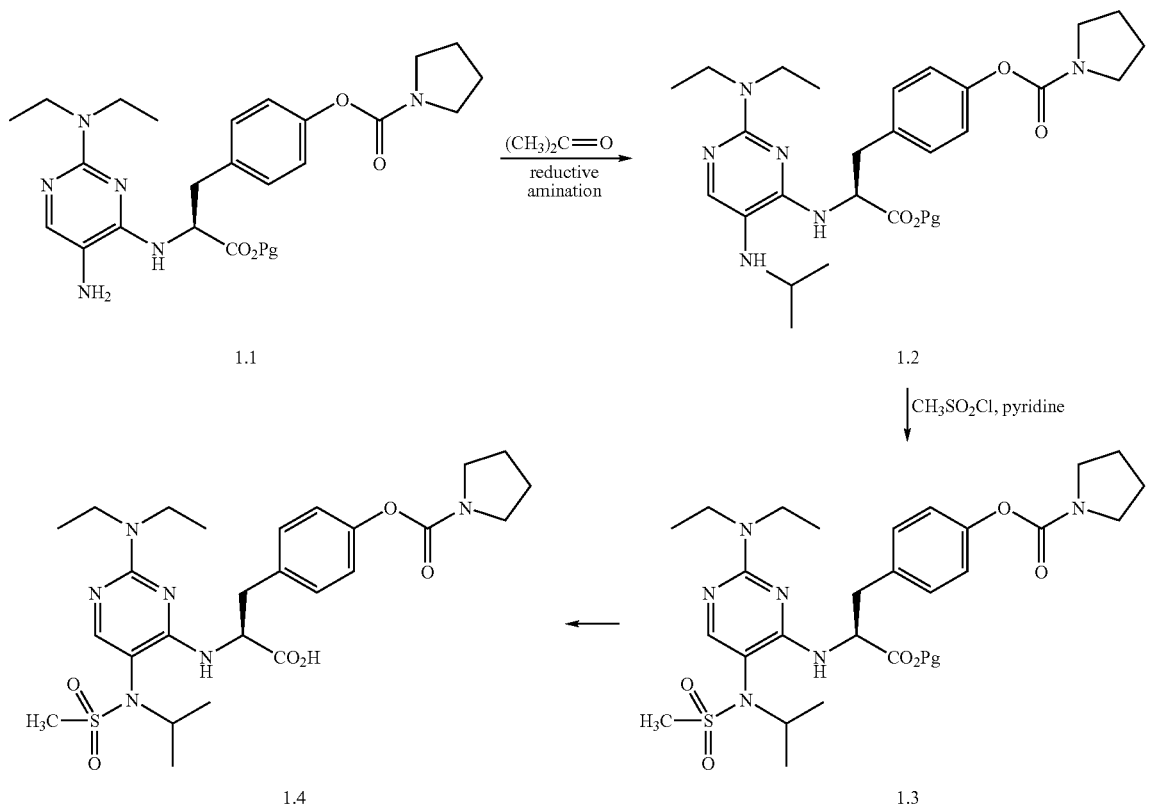

where Pg is a carboxyl protecting group such as benzyl, t-butyl, and the like.

Scheme 1 is particularly useful in the preparation of compounds where $R^2$ is alkyl or cycloalkyl.

In Scheme 1, the starting 5-aminopyrimidine intermediates, compound 1.1, are described in detail in U.S. Pat. No. 7,026,328 B1 and, for the sake of illustration only, are shown in this scheme as 4-substituted phenylalanine derivatives. It is understood, of course, that 2- and 3-substituted phenylalanine derivatives would follow a similar reaction pathway.

Specifically, in Scheme 1,5-amino-2-diethylamino-4-substituted pyrimidine, compound 1.1 (prepared from by corresponding 5-nitro-pyrimidine by reduction with 5% Pd/C or 5% $PtO_2$ by weight) is reacted under conventional reductive amination conditions with a slight excess of a $C_1$-$C_4$ aldehyde or ketone which is Scheme 1 is illustrated by acetone. In Scheme 1, the 5-amino group of compound 1.1 forms an intermediate imine (not shown) which is in situ reduced to the corresponding amine, compound 1.2, by conventional reducing agents such as sodium cyanoborohydride, sodium borohydride, hydrogen over a suitable catalyst such as $PtO_2$, and the like. The reaction is conducted in a suitable inert diluent such as tetrahydrofuran, methylene chloride, and the like. The reaction is maintained at from about 0° C. to about 30° C. until the reaction is substantially complete which typically occurs within about 0.5 to 16 hours. Upon completion of the reaction, the compound 1.2 is recovered by conventional methods including neutralization, evaporation, extraction, precipitation, chromatography, filtration, and the like or, alternatively, is employed in the next step without purification and/or isolation.

Conversion of the amine group in compound 1.2 to the corresponding alkylsulfonylamido group, compound 1.3, proceeds via conventional methods. For example, in one method, compound 1.2 is contacted with a slight excess of an alkanesulfonyl halide, such as methanesulfonyl chloride, in the presence of a suitable base such as triethylamine, diisopropylethylamine and the like in order to scavenge the acid generated. The reaction is preferably conducted in a suitable inert solvent such as tetrahydrofuran, dioxane, chloroform and the like. The reaction is preferably conducted at from about −5° to −30° C. and is continued until the reaction is substantially complete which typically occurs in 0.5 to 16 hours. Upon completion of the reaction, compound 1.3 can be recovered by conventional methods including neutralization, evaporation, extraction, precipitation, chromatography, filtration, and the like or, alternatively, is employed in the next step without purification and/or isolation.

Alkylsulfonyl halides are either known compounds or compounds that can be prepared by convention synthetic procedures. Such compounds are typically prepared from the corresponding sulfonic acid, i.e., from the compounds of the formula $R^1$—$SO_3H$ where $R^1$ is as defined above, using phosphorus trichloride and phosphorus pentachloride. The reaction is generally conducted by contacting the sulfonic acid with about 2 to 5 molar equivalents of phosphorus trichloride or phosphorus pentachloride, either neat or in an inert solvent, such as dichloromethane, at a temperature in the range of 0° C. to about 80° C. for about 1 to about 48 hours to afford the sulfonyl chloride. Alternatively, the sulfonyl chloride can be prepared from the corresponding thiol compound, i.e., from compounds of the formula $R^1$—SH where $R^1$ is as defined above, by treating the thiol with chlorine (Cl$_2$) and water under conventional reaction conditions.

Examples of sulfonyl chlorides for use in this invention include, but are not limited to, methanesulfonyl chloride, ethanesulfonyl chloride, 2-propanesulfonyl chloride, 1-butanesulfonyl chloride, trifluoromethanesulfonyl chloride, 2,2,2-trifluoroethanesulfonyl chloride, and the like.

The carboxyl protecting group of compound 1.3 is then removed by conventional conditions to provide for compound 1.4, a compound of Formula I. In one embodiment, a t-butyl protecting group can be removed by contact with formic acid.

ladium/carbon catalyst typically in a protic solvent such as methanol under elevated hydrogen pressures. Upon completion of the reaction, compound 1.4 can be recovered by conventional methods including neutralization, evaporation, extraction, precipitation, chromatography, filtration, and the like.

In another embodiment, the compounds of this invention can be prepared as described below in Scheme 2:

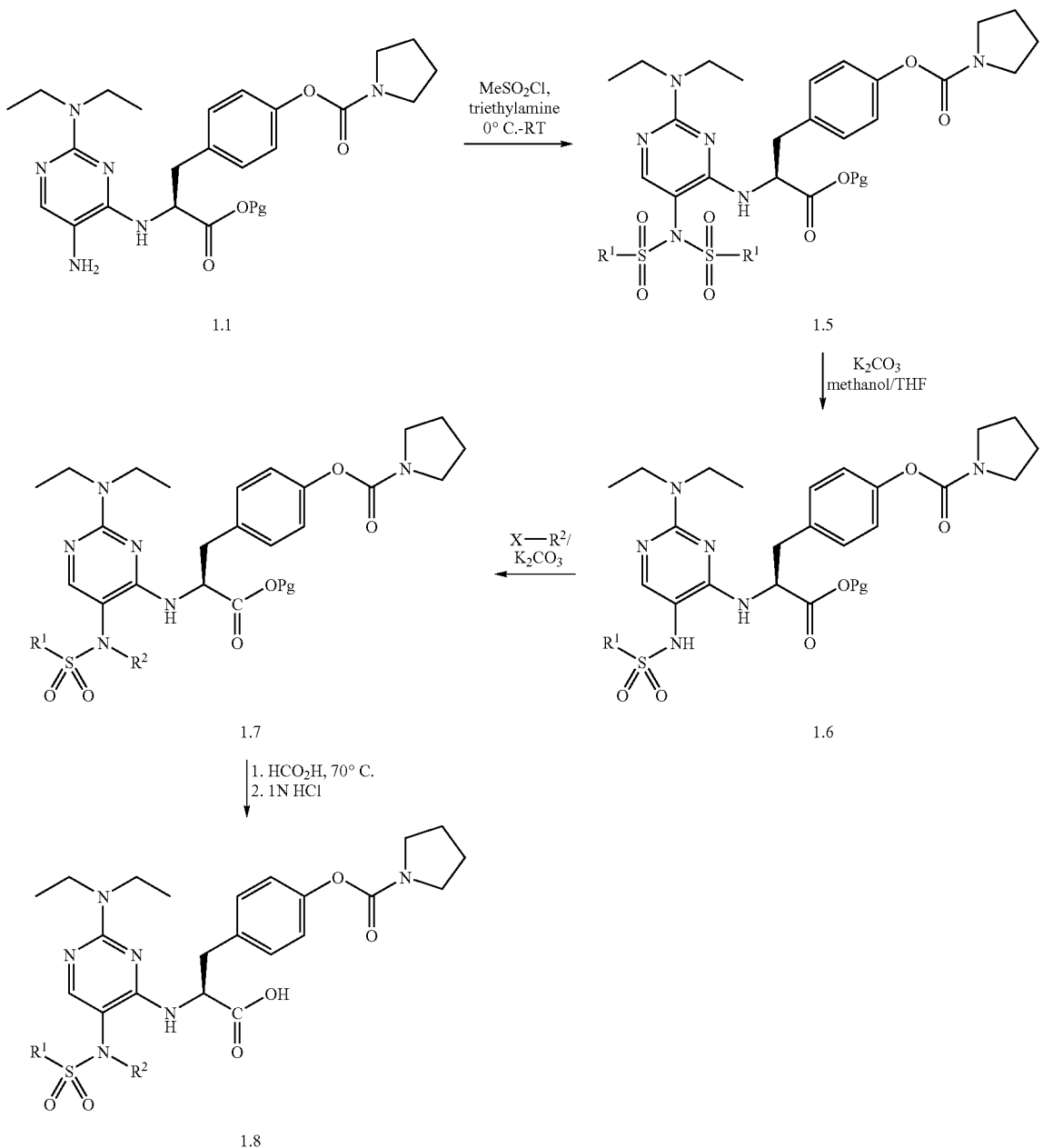

Scheme 2

In another embodiment, a benzyl protecting group can be removed by contact with hydrogen in the presence of a palwhere R$^1$ and R$^2$ is as defined herein; Pg is a carboxyl protecting group and X is halo.

In Scheme 2, the starting 5-aminopyrimidine intermediates, compound 1.1, are described in detail in U.S. Pat. No. 7,026,328 B1 and, for the sake of illustration only, are shown in this scheme as 4-substituted phenylalanine derivatives. It is understood, of course, that 2- and 3-substituted phenylalanine derivatives would follow a similar reaction pathway.

Specifically, in Scheme 2,5-amino-2-diethylamino-4-substituted pyrimidine, compound 1.1 (prepared from by corresponding 5-nitro-pyrimidine by reduction with 5% Pd/C or 5% $PtO_2$ by weight) is reacted with a slight excess of an $R^1$-sulfonyl halide, such as methanesulfonyl chloride, in the presence of a suitable base such as triethylamine, diisopropylethylamine and the like in order to scavenge the acid generated. The reaction is preferably conducted in a suitable inert solvent such as tetrahydrofuran, dioxane, dichloromethane, chloroform and the like. The reaction is preferably conducted at from about −5° to 30° C. and is continued until the reaction is substantially complete which typically occurs in 0.5 to 16 hours. Upon completion of the reaction, compound 1.5 can be recovered by conventional methods including neutralization, evaporation, extraction, precipitation, chromatography, filtration, and the like or, alternatively, is employed in the next step without purification and/or isolation.

Selective removal of a single $R^1SO_2$— group from compound 1.5 proceeds under conventional conditions. For example, reaction of compound 1.5 with base in a protic solvent such as methanol, ethanol, or water, optionally in the presence of THF and the like, e.g. a 1:1 mixture of methanol/tetrahydrofuran or 1:1 mixture of water/tetrahydrofuran provides for compound 1.6. The reaction mixture comprises an excess of a suitable base such as potassium carbonate, sodium carbonate and the like and the reaction is preferably maintained at elevated temperatures such 20° to 60° C. The reaction is continued until substantially complete which typically occurs in 24-144 hours. Upon completion of the reaction, compound 1.6 can be recovered by conventional methods including neutralization, evaporation, extraction, precipitation, chromatography, filtration, and the like or, alternatively, is employed in the next step without purification and/or isolation.

Reaction of compound 1.6 with an excess of an alkyl halide, a dialkyl sulfate, an alkenyl halide, an alkynyl halide, or a cycloalkyl halide (i.e., X—$R^2$— the "halide compound") proceeds under conventional conditions to provide for compound 1.7. The reaction is typically conducted by contacting compound 1.6 with from about 1.1 to 20 equivalent so of the halide compound in an inert diluent such as acetone, chloroform, methylene chloride and the like in the presence of a base such as potassium carbonate, triethylamine and the like to scavenge the acid generated during reaction. The reaction is preferably conducted at from about 20° to 60° C. and is continued until the reaction is substantially complete which typically occurs in 0.1 to 16 hours. Upon completion of the reaction, compound 1.6 can be recovered by conventional methods including neutralization, evaporation, extraction, precipitation, chromatography, filtration, and the like or, alternatively, is employed in the next step without purification and/or isolation.

The carboxyl protecting group of compound 1.7 is then removed by conventional conditions to provide for compound 1.8, a compound of Formula I. In one embodiment, a t-butyl protecting group can be removed by contact with formic acid. In another embodiment, a benzyl protecting group can be removed by contact with hydrogen in the presence of a palladium/carbon catalyst typically in a protic solvent such as methanol under elevated hydrogen pressures. Upon completion of the reaction, compound 1.8 can be recovered by conventional methods including neutralization, evaporation, extraction, precipitation, chromatography, filtration, and the like.

In still another embodiment, the compounds of this invention can be prepared as described below in Scheme 3:

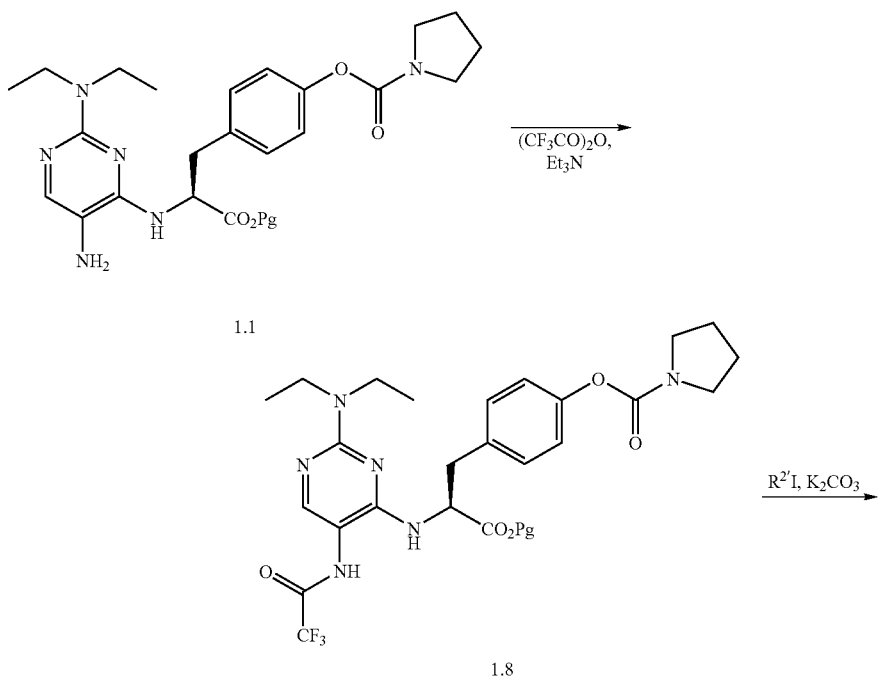

-continued

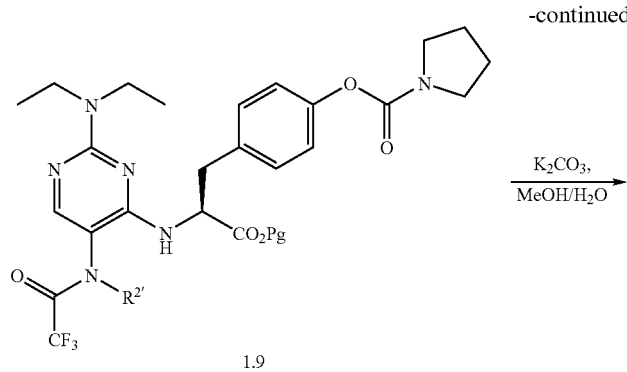

1.9

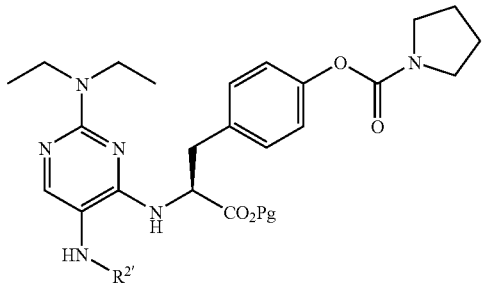

1.10

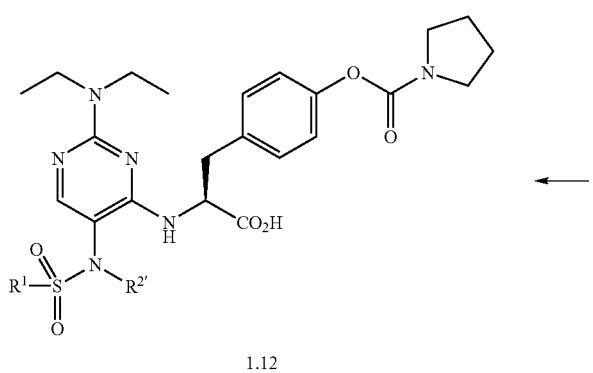

1.12

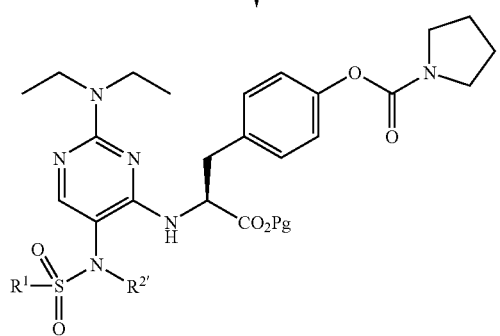

1.11 where $R^1$ is as defined above, Pg is a carboxyl protecting group such as benzyl, t-butyl, and the like and $R^{2'}$ is an alkyl, alkenyl, alkynyl, or phenylalkylene group having a $CH_2$ moiety attached to the iodo group.

In Scheme 1, the starting 5-aminopyrimidine intermediates, compound 1.1, are described in detail in U.S. Pat. No. 7,026,328 B1 and, for the sake of illustration only, are shown in this scheme as 4-substituted phenylalanine derivatives. It is understood, of course, that 2- and 3-substituted phenylalanine derivatives would follow a similar reaction pathway.

Specifically, in Scheme 1,5-amino-2-diethylamino-4-substituted pyrimidine, compound 1.1 (prepared from by corresponding 5-nitro-pyrimidine by reduction with 5% Pd/C or 5% $PtO_2$ by weight) is converted to the corresponding trifluoroacetamide, compound 1.8, by conventional methods. For example, a slight excess of trifluoroacetic anhydride is combined with compound 1.1 in a suitable inert diluent such as tetrahydrofuran, methylene chloride, pyridine, and the like. The reaction is maintained at from about 0° C. to about 30° C. until the reaction is substantially complete which typically occurs within about 0.5 to 24 hours. Upon completion of the reaction, the compound 1.8 is recovered by conventional methods including neutralization, evaporation, extraction, precipitation, chromatography, filtration, and the like or, alternatively, is employed in the next step without purification and/or isolation.

Conversion of compound 1.8 to the corresponding $N(R^{2'})$, N-trifluoroacetamido-pyrimidine, compound 1.9, again proceeds via conventional techniques. For example, an excess of the halide, $R^{2'}$—I, is combined with compound 1.8 in a suitable inert diluent such as DMF in the presence of an excess of a suitable base such as potassium carbonate. In one embodiment, approximately two equivalents of $R^{2'}$—I and potassium carbonate are employed. The reaction is maintained under ambient conditions in a sealed container and is continued until the reaction is substantially complete which typically occurs in 20-72 hours. Upon completion of the reaction, the compound 1.9 is recovered by conventional methods including neutralization, evaporation, extraction, precipitation, chromatography, filtration, and the like or, alternatively, is employed in the next step without purification and/or isolation.

The trifluoroacetyl group is then removed to provide for the corresponding amine, compound 1.10. In this embodiment, the trifluoroacetyl group acts as an amine protecting group. As above, this reaction conventionally proceeds, for example, by contacting compound 1.9 with a large excess of a suitable base such as potassium carbonate in a mixture of water and a protic solvent such as methanol. The reaction is conducted at elevated temperatures such as 40° to 60° C. and is continued until the reaction is substantially complete. Upon completion of the reaction, the compound 1.10 is recovered by conventional methods including neutralization, evaporation, extraction, precipitation, chromatography, filtration, and the like or, alternatively, is employed in the next step without purification and/or isolation.

Next, conversion of the amine group in compound 1.10 to the corresponding alkylsulfonylamido group, compound 1.11, proceeds via conventional methods. For example, in one method, compound 1.10 is contacted with a slight excess of an alkylsulfonyl halide in the presence of a suitable base such as triethylamine, diisopropylethylamine and the like in order to scavenge the acid generated. The reaction is preferably conducted in a suitable inert solvent such as tetrahydrofuran, dioxane, chloroform and the like. The reaction is preferably conducted at from about 0° to 30° C. and is continued until the reaction is substantially complete which typically occurs in 2-48 hours. Upon completion of the reaction, compound 1.11 can be recovered by conventional methods including neutralization, evaporation, extraction, precipitation, chromatography, filtration, and the like or, alternatively, is employed in the next step without purification and/or isolation.

The carboxyl protecting group of compound 1.11 can be removed by conventional conditions to provide for compound 1.12, a compound of Formula I. In one embodiment, a t-butyl protecting group can be removed by contact with formic acid. In another embodiment, a benzyl protecting group can be removed by contact with hydrogen in the presence of a palladium/carbon catalyst typically in a protic solvent such as methanol under elevated hydrogen pressures. Upon completion of the reaction, compound 1.12 can be recovered by conventional methods including neutralization, evaporation, extraction, precipitation, chromatography, filtration, and the like.

The invention also includes esters of the compounds of this invention. The preparation of esters is illustrated in the various schemes described above, such as in scheme 1, (compound 1.3), in scheme 2 (compound 1.7), and in scheme 3 (compound 1.11). Furthermore, Example 1 describes the preparation of (S)-4-(3-tert-butoxy-2-(2-(diethylamino)-5-(N-isopropylmethylsulfonamido)-pyrimidin-4-ylamino)-3-oxopropyl)phenyl pyrrolidine-1-carboxylate, and Example 4 describes the preparation of (S)-4-(3-tert-butoxy-2-(2-(diethylamino)-5-(N-(prop-2-ynyl)methyl-sulfonamido)pyrimidin-4-ylamino)-3-oxopropyl)phenyl pyrrolidine-1-carboxylate. Esters of the acids of this invention can also be prepared from the acids by ways well known in the art. For example, amino acid methyl esters can be prepared using the method of Brenner and Huber, Helv. Chim. Acta 1953, 36, 1109.

Pharmaceutical Formulations

When employed as pharmaceuticals, the compounds of this invention are usually administered in the form of pharmaceutical compositions. These compounds can be administered by a variety of routes including oral, rectal, transdermal, subcutaneous, intravenous, intramuscular, and intranasal. These compounds are effective as both injectable and oral compositions. Such compositions are prepared in a manner well known in the pharmaceutical art and comprise at least one active compound.

This invention also includes pharmaceutical compositions which contain, as the active ingredient, one or more of the compounds of Formula I-II above associated with pharmaceutically acceptable carriers. In making the compositions of this invention, the active ingredient is usually mixed with an excipient, diluted by an excipient or enclosed within such a carrier which can be in the form of a capsule, sachet, paper or other container. The excipient employed is typically an excipient suitable for administration to human subjects or other mammals. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

Administration of therapeutic agents by intravenous formulation is well known in the pharmaceutical industry. An intravenous formulation should possess certain qualities aside from being just a composition in which the therapeutic agent is soluble. For example, the formulation should promote the overall stability of the active ingredient(s), also, the manufacture of the formulation should be cost effective. All of these factors ultimately determine the overall success and usefulness of an intravenous formulation.

Other accessory additives that may be included in pharmaceutical formulations of compounds of the present invention as follow: solvents: ethanol, glycerol, propylene glycol; stabilizers: ethylene diamine tetraacetic acid (EDTA), citric acid; antimicrobial preservatives: benzyl alcohol, methyl paraben, propyl paraben; buffering agents: citric acid/sodium citrate, potassium hydrogen tartrate, sodium hydrogen tartrate, acetic acid/sodium acetate, maleic acid/sodium maleate, sodium hydrogen phthalate, phosphoric acid/potassium dihydrogen phosphate, phosphoric acid/disodium hydrogen phosphate; and tonicity modifiers: sodium chloride, mannitol, dextrose.

The presence of a buffer may be necessary to maintain the aqueous pH in the range of from about 4 to about 8 and more preferably in a range of from about 4 to about 6. The buffer system is generally a mixture of a weak acid and a soluble salt thereof, e.g., sodium citrate/citric acid; or the monocation or dication salt of a dibasic acid, e.g., potassium hydrogen tartrate; sodium hydrogen tartrate, phosphoric acid/potassium dihydrogen phosphate, and phosphoric acid/disodium hydrogen phosphate.

The amount of buffer system used is dependent on (1) the desired pH; and (2) the amount of drug. Generally, the amount of buffer used is in a 0.5:1 to 50:1 mole ratio of buffer:drug (where the moles of buffer are taken as the combined moles of the buffer ingredients, e.g., sodium citrate and citric acid) of formulation to maintain a pH in the range of 4 to 8 and generally, a 1:1 to 10:1 mole ratio of buffer (combined) to drug present is used.

One useful buffer in the invention is sodium citrate/citric acid in the range of 5 to 50 mg per mL of sodium citrate to 1 to 15 mg per mL of citric acid, sufficient to maintain an aqueous pH of 4-6 of the composition.

The buffer agent may also be present to prevent the precipitation of the drug through soluble metal complex formation with dissolved metal ions, e.g., Ca, Mg, Fe, Al, Ba, which may leach out of glass containers or rubber stoppers or be present in ordinary tap water. The agent may act as a competitive complexing agent with the drug and produce a soluble metal complex leading to the presence of undesirable particulates.

In addition, the presence of an agent, e.g., sodium chloride in an amount of about of 1-8 mg/mL, to adjust the tonicity to the same value of human blood may be required to avoid the swelling or shrinkage of erythrocytes upon administration of the intravenous formulation leading to undesirable side effects such as nausea or diarrhea and possibly to associated blood disorders. In general, the tonicity of the formulation matches that of human blood which is in the range of 282 to 288 mOsm/kg, and in general is 285 mOsm/kg, which is equivalent to the osmotic pressure corresponding to a 0.9% solution of sodium chloride.

The intravenous formulation can be administered by direct intravenous injection, i.v. bolus, or can be administered by infusion by addition to an appropriate infusion solution such as 0.9% sodium chloride injection or other compatible infusion solution.

The compositions are preferably formulated in an oral unit dosage form, each dosage containing from about 1 to about 250 mg, more usually from about 5 to about 100 mg, for example about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound is effective over a wide dosage range and is generally administered in a pharmaceutically effective amount. It, will be understood, however, that the amount of the compound actually administered will be determined by a physician, in the light of the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be breathed directly from the nebulizing device or the nebulizing device may be attached to a face masks tent, or intermittent positive pressure breathing machine. Solution, suspension, or powder compositions may be administered, preferably orally or nasally, from devices which deliver the formulation in an appropriate manner.

The following formulation examples illustrate the pharmaceutical compositions of the present invention.

Formulation Example 1

Hard gelatin capsules containing the following ingredients are prepared:

| Ingredient | Quantity (mg/capsule) |
|---|---|
| Active Ingredient | 30.0 |
| Starch | 305.0 |
| Magnesium stearate | 5.0 |

The above ingredients are mixed and filled into hard gelatin capsules in 340 mg quantities.

Formulation Example 2

A tablet formula is prepared using the ingredients below:

| Ingredient | Quantity (mg/tablet) |
|---|---|
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

Formulation Example 3

A dry powder inhaler formulation is prepared containing the following components:

| Ingredient | Weight % |
|---|---|
| Active Ingredient | 5 |
| Lactose | 95 |

The active ingredient is mixed with the lactose and the mixture is added to a dry powder inhaling appliance.

Formulation Example 4

Tablets, each containing 30 mg of active ingredient, are prepared as follows:

| Ingredient | Quantity (mg/tablet) |
| --- | --- |
| Active Ingredient | 30.0 mg |
| Starch | 45.0 mg |
| Microcrystalline cellulose | 35.0 mg |
| Polyvinylpyrrolidone | 4.0 mg |
| (as 10% solution in sterile water) | |
| Sodium carboxymethyl starch | 4.5 mg |
| Magnesium stearate | 0.5 mg |
| Talc | 1.0 mg |

The active ingredient, starch, and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50° C. to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

Formulation Example 5

Capsules, each containing 40 mg of medicament are made as follows:

| Ingredient | Quantity (mg/capsule) |
| --- | --- |
| Active Ingredient | 40.0 mg |
| Starch | 109.0 mg |
| Magnesium stearate | 1.0 mg |
| Total | 150.0 mg |

The active ingredient, starch and magnesium stearate are blended, passed through a No. 20 mesh U.S. sieve, and filled into hard gelatin capsules in 150 mg quantities.

Formulation Example 6

Suppositories, each containing 25 mg of active ingredient are made as follows:

| Ingredient | Amount |
| --- | --- |
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation Example 7

Suspensions, each containing 50 mg of medicament per 5.0 ml dose are made as follows:

| Ingredient | Amount |
| --- | --- |
| Active Ingredient | 50.0 mg |
| Xanthan gum | 4.0 mg |
| Sodium carboxymethyl cellulose (11%) | 50.0 mg |
| Microcrystalline cellulose (89%) | |
| Sucrose | 1.75 g |
| Sodium benzoate | 10.0 mg |
| Flavor and Color | q.s. |
| Purified water to | 5.0 mL |

The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Formulation Example 8

| Ingredient | Quantity (mg/capsule) |
| --- | --- |
| Active Ingredient | 15.0 mg |
| Starch | 407.0 mg |
| Magnesium stearate | 3.0 mg |
| Total | 425.0 mg |

The active ingredient, starch, and magnesium stearate are blended, passed through a No. 20 mesh U.S. sieve, and filled into hard gelatin capsules in 425.0 mg quantities.

Formulation Example 9

A subcutaneous formulation may be prepared as follows:

| Ingredient | Quantity |
| --- | --- |
| Active Ingredient | 5.0 mg |
| Corn Oil | 1.0 mL |

Formulation Example 10

An intravenous formulation may be prepared as follows:

| Ingredient | Quantity |
| --- | --- |
| Active Ingredient | 250 mg |
| Isotonic saline | 1000 mL |

Another formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system used for the transport of biological factors to specific anatomical regions of the body is described in U.S. Pat. No. 5,011,472, which is herein incorporated by reference.

Indirect techniques, usually involve formulating the compositions to provide for drug latentiation by the conversion of hydrophilic drugs into lipid-soluble drugs. Latentiation is generally achieved through blocking of the hydroxyl, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions, which can transiently open the blood-brain barrier.

Other suitable formulations for use in the present invention can be found in Remington's Pharmaceutical Sciences, Mace Publishing Company, Philadelphia, Pa., 17th ed. (1985).

As noted above, the compounds described herein are suitable for use in a variety of drug delivery systems described above. Additionally, in order to enhance the in vivo serum half-life of the administered compound, the compounds may be encapsulated, introduced into the lumen of liposomes, prepared as a colloid, or other conventional techniques may be employed which provide an extended serum half-life of the compounds. A variety of methods are available for preparing liposomes, as described in, e.g., Szoka, et al., U.S. Pat. Nos. 4,235,871, 4,501,728 and 4,837,028 each of which is incorporated herein by reference.

Compounds having the desired biological activity may be modified as necessary to provide desired properties such as improved pharmacological properties (e.g., in vivo stability, bio-availability), or the ability to be detected in diagnostic applications. Stability can be assayed in a variety of ways such as by measuring the half-life of the proteins during incubation with peptidases or human plasma or serum. A number of such protein stability assays have been described (see, e.g., Verhoef et al., Eur. J. Drug Metab. Pharmacokinet., 1990, 15(2):83-93).

The conjugates of this invention are VLA-4 antagonists and are contemplated to provide enhanced in vivo retention as compared to the non-conjugated compounds. Such improved retention of the conjugate within the body would result in lower required dosages of the drug, which, in turn, would result in fewer side effects and reduced likelihood of toxicity. In addition, the drug formulation may be administered less frequently to the patient while achieving a similar or improved therapeutic effect.

The conjugates of this invention are anticipated to exhibit inhibition, in vivo, of adhesion of leukocytes to endothelial cells mediated by VLA-4 by competitive binding to VLA-4. Preferably, the compounds of this invention can be used in intravenous formulations for the treatment of diseases mediated by VLA-4 or leukocyte adhesion. Such diseases include inflammatory diseases in mammalian patients such as asthma, Alzheimer's disease, atherosclerosis, AIDS dementia, diabetes (including acute juvenile onset diabetes), inflammatory bowel disease (including ulcerative colitis and Crohn's disease), multiple sclerosis, rheumatoid arthritis, tissue transplantation, tumor metastasis, meningitis, encephalitis, stroke, and other cerebral traumas, nephritis, retinitis, atopic dermatitis, psoriasis, myocardial ischemia and acute leukocyte-mediated lung injury such as that which occurs in adult respiratory distress syndrome. The formulations of the present invention are especially useful in the treatment of inflammatory bowel disease, such as Crohn multiple sclerosis and rheumatoid arthritis.

Appropriate in vivo models for demonstrating efficacy in treating inflammatory conditions include EAE (experimental autoimmune encephalomyelitis) in mice, rats, guinea pigs or primates, as well as other inflammatory models dependent upon $\alpha_4$ integrins.

Inflammatory bowel disease or "IBD" refers to the group of disorders that cause the intestines to become inflamed, generally manifested with symptoms including abdominal cramps and pain, diarrhea, weight loss and intestinal bleeding. IBD is a collective term for two similar diseases ulcerative colitis ("UC") and Crohn's disease ("CD")

Crohn's disease ("CD") is a chronic autoimmune disorder that results in inflammation of the gastrointestinal (GI) tract. Although any area of the GI tract may be involved, CD most commonly affects the small intestine and/or colon. In Crohn's disease, all layers of the intestine may be involved, and there can be normal healthy bowel in between patches of diseased bowel. CD is associated with fibrosis, stenosis and fissuring, fistulae between disease tracts and adjacent structures (i.e., bladder, other bowel segments, skin) and abscess. CD patients are typically present with diarrhea, abdominal pain and weight loss. The abdominal pain usually is insidious and may be associated with a tender, inflammatory mass. Fever, weight loss, stomatitis, perianal fistulae and/or fissure, arthritis, and erythema nodosum are all commonly seen. There is considerable morbidity associated with CD, particularly in patients with disease not controlled by currently available drugs. Up to 75% of patients with moderate to severe disease require surgery and up to 75% of these patients will experience post surgical disease recurrence within 10 years and up to 50% will undergo a repeat surgery within 20 years. This high rate of recurrence indicates a need for new effective treatments for forth active disease and maintenance of disease remission.

Ulcerative colitis or "UC" is a chronic, episodic, inflammatory disease of the large intestine and rectum characterized by bloody diarrhea. Ulcerative colitis is an inflammatory response limited largely to the colonic mucosa and submucosa. Ulcerative colitis can be categorized according to location: "proctitis" involves only the rectum, "proctosigmoiditis" affects the rectum and sigmoid colon, "left-sided colitis" encompasses the entire left side of the large intestine, "pancolitis" inflames the entire colon. Lymphocytes and macrophages are numerous in lesions of inflammatory bowel disease and may contribute to inflammatory injury. An exemplary animal model of inflammatory bowel disease (IBD) is carried out with HLA-B27 transgenic rats. These rats overexpress the human HLA-B27 molecule (heavy chain and beta globulin gene) that is associated with spondyloarthropathies, a group of inflammatory conditions affecting the skeleton. Prior to onset of skeletal inflammatory changes these animals develop non-granulomatous inflammation in the small intestine and diffuse crypt abscesses on the colon, a pathology that is similar to that of Crohn's Disease in humans. Efficacy studies were performed in the HLA-B27 transgenic rat IBD model with compounds of this invention as described in Example J below.

Asthma is a disease characterized by increased responsiveness of the tracheobronchial tree to various stimuli potentiating paroxysmal constriction of the bronchial airways. The stimuli cause release of various mediators of inflammation from IgE-coated mast cells including histamine, eosinophilic and neutrophilic chemotactic factors, leukotrines, prostaglandin and platelet activating factor. Release of these factors recruits basophils, eosinophils and neutrophils, which cause inflammatory injury.

Some appropriate animal models for the in vivo study of asthma may include the rat asthma model, the mouse asthma model and the sheep model as described in Example E.

Atherosclerosis is a disease of arteries (e.g., coronary, carotid, aorta and iliac). The basic lesion, the atheroma, consists of a raised focal plaque within the intima, having a core of lipid and a covering fibrous cap. Atheromas compromise arterial blood flow and weaken affected arteries. Myocardial and cerebral infarcts are a major consequence of this disease. Macrophages and leukocytes are recruited to atheromas and contribute to inflammatory injury.

Rheumatoid arthritis is a chronic, relapsing inflammatory disease that primarily causes impairment and destruction of joints. Rheumatoid arthritis usually first affects the small joints of the hands and feet but then may involve the wrists, elbows, ankles and knees. The arthritis results from interaction of synovial cells with leukocytes that infiltrate from the circulation into the synovial lining of the joints. See e.g., Paul, Immunology (3d ed., Raven Press, 1993). Over time, bone erosion, destruction of cartilage, and complete loss of joint integrity can occur. Eventually, multiple organ systems may be affected.

Joint damage in rheumatoid arthritis begins with the proliferation of synovial macrophages and fibroblasts after a triggering incident, possibly autoimmune or infectious. Lymphocytes infiltrate perivascular regions, and endothelial cells proliferate. Neovascularization then occurs. Blood vessels in the affected joint become occluded with small clots of inflammatory cells. Over time, inflamed synovial tissue begins to grow irregularly, forming invasive pannus tissue. Pannus invades and destroys cartilage and bone. Multiple cytokines, interleukins, proteinases, and growth factors are released, causing further joint destruction and the development of systemic complications. See, Firestein G. S. Etiology and pathogenesis of rheumatoid arthritis, Ruddy S, Harris E D, Sledge C B, Kelley W N, eds. Kelley's Textbook of Rheumatology, 7th ed. Philadelphia: W.B. Saunders, 2005:996-1042.

Appropriate animal models for the study of rheumatoid arthritis may include Adjuvant Induced Arthritis ("AIA") and Collagen Induced Arthritis ("CIA") as described in Examples G and H herein.

Another indication for the compounds of this invention is in the treatment of organ or graft rejection mediated by VLA-4. Over recent years there has been a considerable improvement in the efficiency of surgical techniques for transplanting tissues and organs such as skin, kidney, liver, heart, lung, pancreas and bone marrow. Perhaps the principal outstanding problem is the lack of satisfactory agents for inducing immunotolerance in the recipient to the transplanted allograft or organ. When allogeneic cells or organs are transplanted into a host (i.e., the donor and donee are different individuals from the same species), the host immune system is likely to mount an immune response to foreign antigens in the transplant (host-versus-graft disease) leading to destruction of the transplanted tissue. CD8$^+$ cells, CD4 cells and monocytes are all involved in the rejection of transplant tissues. Compounds of this invention which bind to alpha-4 integrin are useful, inter alia, to block alloantigen-induced immune responses in the donee thereby preventing such cells from participating in the destruction of the transplanted tissue or organ. See, e.g., Paul et al., *Transplant International* 9, 420-425 (1996); Georczynski et al., *Immunology* 87, 573-580 (1996); Georcyznski et al., *Transplant. Immunol.* 3, 55-61 (1995); Yang et al., *Transplantation* 60, 71-76 (1995); Anderson et al., *APMIS* 102, 23-27 (1994).

A related use for compounds of this invention, which bind to VLA-4 is in modulating the immune response involved in "graft versus host" disease ("GVHD"). See e.g., Schlegel et al., *J. Immunol.* 155, 3856-3865 (1995). GVHD is a potentially fatal disease that occurs when immunologically competent cells are transferred to an allogeneic recipient. In this situation, the donor's immunocompetent cells may attack tissues in the recipient. Tissues of the skin, gut epithelia and liver are frequent targets and may be destroyed during the course of GVHD. The disease presents an especially severe problem when immune tissue is being transplanted, such as in bone marrow transplantation; but less severe GVHD has also been reported in other cases as well, including heart and liver transplants. The therapeutic agents of the present invention are used, inter alia, to block activation of the donor T-cells thereby interfering with their ability to lyse target cells in the host.

A further use of the compounds of this invention is inhibiting tumor metastasis. Several tumor cells have been reported to express VLA-4 and compounds, which bind VLA-4 block adhesion of such cells to endothelial cells. Steinback et al., *Urol. Res.* 23, 175-83 (1995); Orosz et al., *Int. J. Cancer* 60, 867-71 (1995); Freedman et al., *Leuk. Lymphoma* 13, 47-52 (1994); Okahara et al., *Cancer Res.* 54, 3233-6 (1994).

A further use of the compounds of this invention is in treating multiple sclerosis. Multiple sclerosis is a progressive neurological autoimmune disease that affects an estimated 250,000 to 350,000 people in the United States. Multiple sclerosis is thought to be the result of a specific autoimmune reaction in which certain leukocytes attack and initiate the destruction of myelin, the insulating sheath covering nerve fibers. In an animal model for multiple sclerosis, murine monoclonal antibodies directed against VLA-4 have been shown to block the adhesion of leukocytes to the endothelium, and thus prevent inflammation of the central nervous system and subsequent paralysis in the animals.[16]

Pharmaceutical compositions of the invention are suitable for use in a variety of drug delivery systems. Suitable formulations for use in the present invention are found in *Remington's Pharmaceutical Sciences*, Mace Publishing Company, Philadelphia, Pa., 17th ed. (1985).

The amount administered to the patient will vary depending upon what is being administered, the purpose of the administration, such as prophylaxis or therapy, the state of the patient, the manner of administration, and the like. In therapeutic applications, compositions are administered to a patient already suffering from a disease in an amount sufficient to cure or at least partially arrest the symptoms of the disease and its complications. An amount adequate to accomplish this is defined as "therapeutically effective dose." Amounts effective for this use will depend on the disease condition being treated as well as by the judgment of the attending clinician depending upon factors such as the severity of the inflammation, the age, weight and general condition of the patient, and the like, with reference to the appropriate animal model data, such as that provided herein. Methods for estimating appropriate human dosages, based on such data, are known in the art. (see, for example, Wagner, J. G. Pharmacokinetics for the Pharmaceutical Scientist. Technomic, Inc., Lancaster, Pa. 1993).

The compositions administered to a patient are in the form of pharmaceutical compositions described above. These compositions may be sterilized by conventional sterilization techniques, or may be sterile filtered. The resulting aqueous solutions may be packaged for use as is, or lyophilized, the lyophilized preparation being combined with a sterile aqueous carrier prior to administration.

Compounds having the desired biological activity may be modified as necessary to provide desired properties such as improved pharmacological properties (e.g., in vivo stability, bio-availability), or the ability to be detected in diagnostic applications. Stability can be assayed in a variety of ways such as by measuring the half-life of the proteins during incubation with peptidases or human plasma or serum. A number of such protein stability assays have been described (see, e.g., Verhoef et al., Eur. J. Drug Metab. Pharmacokinet., 1990, 15(2):83-93).

The therapeutic dosage of the compounds of the present invention will vary according to, for example, the particular use for which the treatment is made, the manner of administration of the compound, the health and condition of the patient, and the judgment of the prescribing physician. For example, for intravenous administration, the dose will typically be in the range of about 20 µg to about 2000 µg per kilogram body weight, preferably about 20 µg to about 500 µg, more preferably about 100 µg to about 300 µg per kilogram body weight. Suitable dosage ranges for intranasal administration are generally about 0.1 µg to 1 mg per kilogram body weight. Effective doses can be extrapolated from dose-response curves derived from in vitro or animal model test systems.

Compounds of this invention are also capable of binding or antagonizing the actions of $\alpha_4\beta_1$, and $\alpha_4\beta_7$ integrins. Accordingly, compounds of this invention are also useful for preventing or reversing the symptoms, disorders or diseases induced by the binding of these integrins to their respective ligands.

In another aspect of the invention, the compounds and compositions described herein can be used to inhibit immune cell migration from the bloodstream to the central nervous system in the instance of, for example, multiple sclerosis, or to areas which result in inflammatory-induced destruction of the myelin. Preferably, these reagents inhibit immune cell migration in a manner that inhibits demyelination and that further may promote remyelination. The reagents may also prevent demyelination and promote remyelination of the central nervous system for congenital metabolic disorders in which infiltrating immune cells affect the development myelin sheath, mainly in the CNS. The reagents preferably also reduce paralysis when administered to a subject with paralysis induced by a demyelinating disease or condition.

Inflammatory diseases that are included for treatment by the compositions, compounds and methods disclosed herein include generally conditions relating to demyelination. Histologically, myelin abnormalities are either demyelinating or dysmyelinating. Demyelination implies the destruction of myelin. Dysmyelination refers to defective formation or maintenance of myelin resulting from dysfunction of the oligodendrocytes. Preferably, the compositions and methods disclosed herein are contemplated to treat diseases and conditions relating to demyelination and aid with remyelination. Additional diseases or conditions contemplated for treatment include meningitis, encephalitis, and spinal cord injuries and conditions generally which induce demyelination as a result of an inflammatory response.

The compositions, compounds and cocktails disclosed herein are contemplated for use in treating conditions and diseases associated with demyelination. Diseases and conditions involving demyelination include, but are not limited to, multiple sclerosis, congenital metabolic disorders (e.g., phenylketonuria (PKU), Tay-Sachs disease, Niemann-Pick disease, Gaucher's disease, Hurler's syndrome, Krabbe's disease and other leukodystrophies that impact the developing sheath), neuropathies with abnormal myelination (e.g., Guillain Barre, chronic immune demyelinating polyneuropathy (CIDP), multifocal CIDP, Multifocal Motor Neuropathy (MMN), anti-MAG (Myelin-Associated Glycoprotein) syndrome, GALOP (Gait disorder, Autoantibody, Late-age, Onset, Polyneuropathy) syndrome, anti-sulfatide antibody syndrome, anti-GM2 antibody syndrome, POEMS (Polyneuropathy, Organomegaly, Endocrinopathy, M-Protein and Skin changes) syndrome also known as Crow-Fukase Syndrome and Takatsuki disease, perineuritis, IgM anti-GD1b antibody syndrome), drug related demyelination (e.g., caused by the administration of chloroquine, FK506, perhexyline, procainamide, and zimeldine), other hereditary demyelinating conditions (e.g., carbohydrate-deficient glycoprotein, Cockayne's syndrome, congenital hypomyelinating, congenital muscular dystrophy, Farber's disease, Marinesco-Sjögren syndrome, metachromatic leukodystrophy, Pelizaeus-Merzbacher disease, Refsum disease, prion related conditions, and Salla disease) and other demyelinating conditions (e.g., meningitis, encephalitis (also known as acute disseminated encephalomyelitis, ADEM), or spinal cord injury) or diseases.

There are various disease models that can be used to study these diseases in vivo. For example, animal models include but are not limited to:

TABLE 4

| Disease Model | Species |
| --- | --- |
| EAE | Mouse, rat, guinea pig |
| Myelin-oligodendrocyte glycoprotein (MOG) induced EAE | Rat |
| TNF-α transgenic model of demyelination | Mouse |

The most common demyelinating disease is multiple sclerosis ("MS"), but many other metabolic and inflammatory disorders result in deficient or abnormal myelination. MS is a chronic neurologic disease, which appears in early adulthood and progresses to a significant disability in most cases. There are approximately 350,000 cases of MS in the United States alone. Outside of trauma, MS is the most frequent cause of neurologic disability in early to middle adulthood.

The cause of MS is yet to be determined. MS is characterized by chronic inflammation, demyelination and gliosis (scarring). Demyelination may result in either negative or positive effects on axonal conduction. Positive conduction abnormalities include slowed axonal conduction, variable conduction block that occurs in the presence of high-but not low-frequency trains of impulses or complete conduction block. Positive conduction abnormalities include ectopic impulse generation, spontaneously or following mechanical stress and abnormal "cross-talk" between demyelinated exons.

T cells reactive against myelin proteins, either myelin basic protein (MBP) or myelin proteolipid protein (PLP) have been observed to mediate CNS inflammation in experimental allergic encephalomyelitis. Patients have also been observed as having elevated levels of CNS immunoglobulin (Ig). It is further possible that some of the tissue damage observed in MS is mediated by cytokine products of activated T cells, macrophages or astrocytes.

Today, 80% patients diagnosed with MS live 20 years after onset of illness. Therapies for managing MS include: (1) treatment aimed at modification of the disease course, including treatment of acute exacerbation and directed to long-term suppression of the disease; (2) treatment of the symptoms of MS; (3) prevention and treatment of medical complications; and (4) management of secondary personal and social problems.

The onset of MS may be dramatic or so mild as to not cause a patient to seek medical attention. The most common symptoms include weakness in one or more limbs, visual blurring due to optic neuritis, sensory disturbances, diplopia and ataxia. The course of disease may be stratified into three general categories: (1) relapsing MS, (2) chronic progressive MS, and (3) inactive MS. Relapsing MS is characterized by recurrent attacks of neurologic dysfunction. MS attacks generally evolve over days to weeks and may be followed by complete, partial or no recovery. Recovery from attacks generally occurs within weeks to several months from the peak of symptoms, although rarely some recovery may continue for 2 or more years.

Chronic progressive MS results in gradually progressive worsening without periods of stabilization or remission. This form develops in patients with a prior history of relapsing MS, although in 20% of patients, no relapses can be recalled. Acute relapses also may occur during the progressive course.

A third form is inactive MS. Inactive MS is characterized by fixed neurologic deficits of variable magnitude. Most patients with inactive MS have an earlier history of relapsing MS.

Disease course is also dependent on the age of the patient. For example, favourable prognostic factors include early onset (excluding childhood), a relapsing course and little residual disability 5 years after onset. By contrast, poor prognosis is associated with a late age of onset (i.e., age 40 or older) and a progressive course. These variables are interdependent, since chronic progressive MS tends to begin at a later age that relapsing MS. Disability from chronic progressive MS is usually due to progressive paraplegia or quadriplegia (paralysis) in patients. In one aspect of the invention, patients will preferably be treated when the patient is in remission rather then in a relapsing stage of the disease.

Short-term use of either adrenocorticotropic hormone or oral corticosteroids (e.g., oral prednisone or intravenous methylprednisolone) is the only specific therapeutic measure for treating patients with acute exacerbation of MS.

Newer therapies for MS include treating the patient with interferon beta-1b, interferon beta-1a, and Copaxone® (formerly known as copolymer 1). These three drugs have been shown to significantly reduce the relapse rate of the disease. These drugs are self-administered intramuscularly or subcutaneously.

However, none of the current treatment modalities inhibit demyelination, let alone promotes or allows spontaneous remyelination or reduces paralysis. One aspect of the invention contemplates treating MS with agents disclosed herein either alone or in combination with other standard treatment modalities.

Radiation also can induce demyelination. Central nervous system (CNS) toxicity due to radiation is believed to be cause by (1) damage to vessel structures, (2) deletion of oligodendrocyte-2 astrocyte progenitors and mature oligodendrocytes, (3) deletion of neural stem cell populations in the hippocampus, cerebellum and cortex, and generalized alterations of cytokine expression. Most radiation damage results from radiotherapies administered during the treatment of certain cancers. See for review Belka et al., 2001 *Br. J. Cancer* 85: 1233-9. However, radiation exposure may also be an issue for astronauts (Hopewell, 1994 *Adv. Space Res.* 14: 433-42) as well as in the event of exposure to radioactive substances.

These conditions and diseases are also contemplated for palliative or ameliorating treatments.

EXAMPLES

The following synthetic and biological examples are offered to illustrate this invention and are not to be construed in any way as limiting the scope of this invention. Unless otherwise stated, all temperatures are in degrees Celsius. In the examples below, the following abbreviations have the following meanings. If an abbreviation is not defined, it has its generally accepted meaning.

Å=Angstroms
br s=broad singlet
BSA=bovine serum albumin
d=doublet
dd=doublet of doublets
dq=doubet of quartets
dsextet=doublte of sextets
DMF=dimethylformamide
$EC_{50}$=The dosage at which the desired response is present for 50 percent of the population
EDTA=ethylenediamine tetraacetic acid
EtOAc=ethyl acetate
EtOH=ethanol
$Et_3N$=triethylamine
EM=wavelength of emission (in nm)
EX=wavelength of excitation (in nm)
g=gram
HBSS=Hank's balanced salt solution
HEPES=4-(2-hydroxyethyl)-1-piperazineethanesulfonic acid
HPLC=high performance liquid chromatography
hrs or h=hours
$IC_{50}$=the concentration of an inhibitor that is required for 50% inhibition of an enzyme in vitro
in.=inch
i.p.=intraperitoneally
i-PrOH=iso-propanol
kg=kilogram
L=liters
LC/MS=liquid chromatography/mass spectroscopy
m=multiplet
$m^2$=square meters
M=molar
mbar=millibar
mg=milligram
MHz=megahertz
min.=minutes
mL=milliliters
mm=millimeters
mM=millimolar
mmol=millimoles
mOsm=milliosmol
MTBE=methyl tert-butylether
m/z or M/Z=mass to charge ratio
N=normal
ng=nanograms
nm=nanometers
NMR=nuclear magnetic resonance
PBS=phosphate buffered saline
PBS++=PBS with calcium and magnesium
ppm=parts per million
psi=pounds per square inch p.o.=per os, literally "by mouth", includes oral gavage
q=quartet
q.s.=sufficient amount
$R_f$=retention factor (ratio of distance traveled by substance/distance traveled by solvent front)
rpm=rotations per minute
rt or RT=room temperature
$R_t$=retention time
s=singlet
t=triplet
TFA=trifluoroacetic acid THF=tetrahydrofuran
TLC=thin layer chromatography
UV=ultraviolet
wt/wt=weight to weight ratio
w/v=weight to volume ratio
μg=micrograms
μm=microns
μM=micromolar Example 1

Preparation of (S)-2-(2-(diethylamino)-5-(N-isopropylmethylsulfonamido)pyrimidin-4-ylamino)-3-(4-(pyrrolidine-1-carbonyloxy)phenyl)propanoic acid The synthetic protocol employed in Example 1 is summarized in Scheme 4 illustrated below:

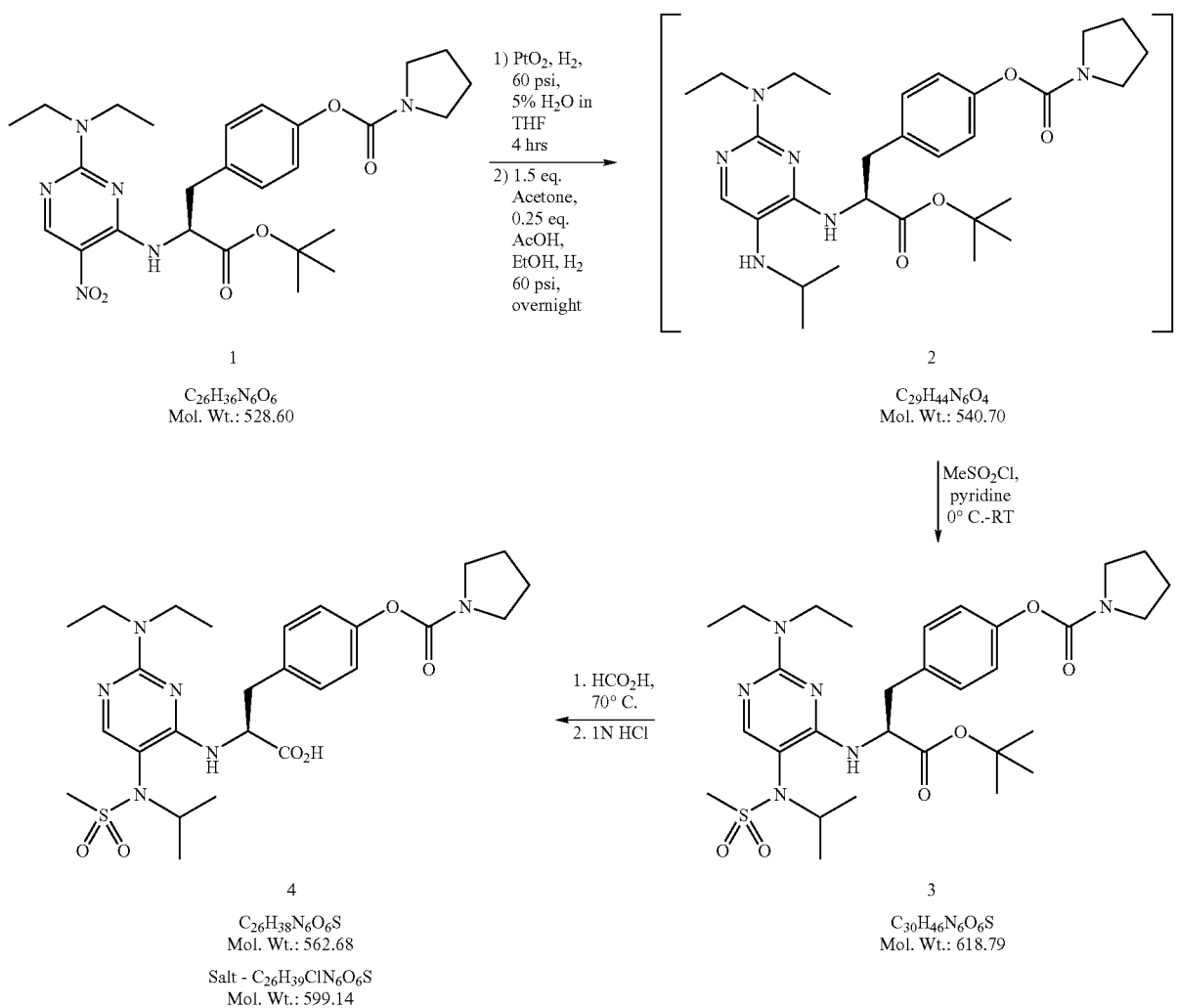

In Scheme 4, compound 4 was prepared in a three pot sequence from the 5-nitropyrmidine compound 1. The synthetic protocol of Scheme 4 significantly simplifies the preparation of this compound by one or more of the following:

1) a substantially accelerated nitro group reduction step;

2) a streamlined reduction/reductive amination sequence that is performed in the same flask with the same solvent and the same catalyst, so manipulations are reduced and exposure of the oxygen sensitive products to air is minimized;

3) the conditions for the reductive amination step minimizes generation of a bis-isopropylamino pyrimidine side product thereby eliminating the need for a chromatographic purification of compound 3;

4) conditions are described whereby it is possible to purify the mono-isopropylaminopyrimidine intermediate, compound 2, by trituration of the corresponding L-tartaric acid salt (though the need for this discrete purification of compound 2 also has been rendered unnecessary by the improvements in the reductive amination step), and 5) conditions for the discrete purification of compound 3 by crystallization from MTBE-hexane or MTBE-cyclohexane have been identified.

In the reaction steps of Scheme 4, flash chromatography was performed using a Biotage Flash 75L, using 800 g KP-Sil silica cartridges (32-63 μM, 60 angstrom, 500-550 m²/g). $R_f$s are reported for analytical thin layer chromatography, using EM Sciences Silica Gel 60 F(254), 250 μM thick plates for normal phase. NMR spectra were obtained on a Varian Gemini 300 MHz spectrometer (300 MHz for $^1$H spectra and 75 MHz for $^{13}$C spectra). Analytical HPLC was performed on an Agilent 1100 Series HPLC with a Phenomenex Luna, 3 μm, C-18, 30×4.6 mm column. The detector was UV at 210 nm. Solvents were 0.1% TFA in water and 0.1% TFA in acetonitrile. The standard flow rate was 1.5 mL/min. and the standard method was named M1 with the solvent gradient changing from 20% CH$_3$CN to 70% CH$_3$CN over 2.33 minutes. An alternate method was named M2 with a flow rate of 2 mL/min. and a gradient changing from 20% CH$_3$CN to 70% CH$_3$CN over 1.75 minutes. Method M15 had a flow rate of 1.5 ml/min. with the solvent composition changing from 20% CH$_3$CN to 70% CH$_3$CN over 10 min., holding at 70% for 2 min., then ramping to 95% over 1 min. and holding at 95% for 2 minutes. LC/MS was performed on an Agilent 1100 Series HPLC with a Series 1100 MSD with electrospray ionization (unless otherwise indicated as chemical ionization). The column and conditions were matched to the free standing HPLC.

Step 1: Preparation of (S)-4-(3-tert-butoxy-2-(2-(diethylamino)-5-(isopropylamino)pyrimidin-4-ylamino)-3-oxopropyl)phenyl pyrrolidine-1-carboxylate (2)

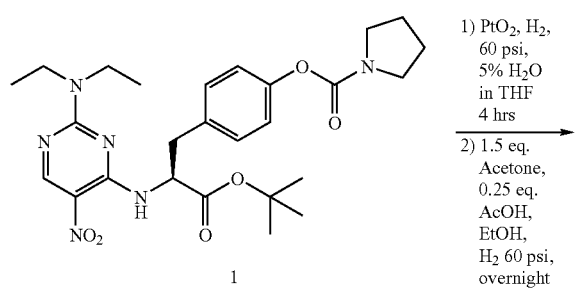

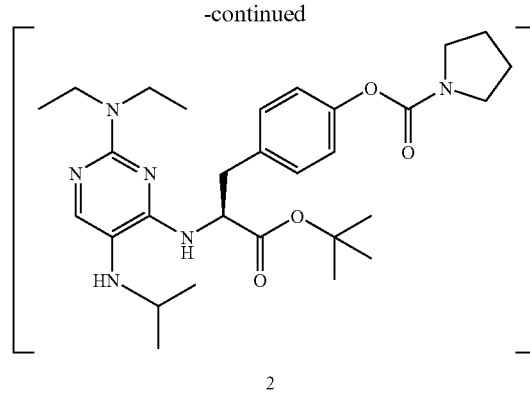

Nitropyrimidine-carbamate 1 (100 g, 189 mmol) and PtO$_2$ (6.33 g, 27.85 mmol) were suspended in 360 mL of wet THF (5% H$_2$O). The mixture was stirred at room temperature under hydrogen (60 psi). After 3 hours, TLC (50% EtOAc/hexanes on silica gel) indicated complete reduction of the nitro group (TLC analysis on silica with EtOAc showed $R_f$=0.2 (streaky) for the amino-pyrimidine and $R_f$=0.86 for the starting nitropyrimidine-carbamate.) In this regard, the use of PtO$_2$ for both steps in this two-step process permitted a one-pot reaction with that added feature that the rate of reduction of the nitro group was dramatically accelerated. In any event, care be taken to minimize exposure to air/oxygen as the aminopyrimidine product is prone to oxidation.

Ethanol (200 mL), acetone (21 mL, 1.5 eq.), and glacial acetic acid (3.0 mL, 0.28 eq.) were added to the aminopyrimidine solution in the hydrogenation flask. After evacuating and purging, the flask was pressurized with H$_2$ (60 psi). The reductive amination was allowed to proceed overnight. TLC on silica using EtOAc as the eluant gave an $R_f$=0.41 (streaky) for the isopropylamino-pyrimidine and an $R_f$=0.11 for the starting aminopyrimidine carbamate. Both TLC and LC/MS confirmed complete reaction with virtually no bis-isopropylaminopyrimidine produced. If necessary, HPLC can be used as an alternative means to monitor progress of the reaction. The crude reaction solution was diluted with EtOAc (1 L) and filtered through a pad of basic alumina (400 mL). The alumina was rinsed with EtOAc (200 mL) and EtOH (200 mL) and the combined organic solutions were concentrated in vacuo. The flask was vented under N$_2$. The viscous oil was redissolved in anhydrous toluene (700 mL) and concentrated. After venting the flask under nitrogen, the product was dried again by azeotropic removal of another 400 mL of toluene. A viscous reddish-brown oil was obtained.

As evidenced by the LC/MS, very little bis-isopropylaminopyrimidine carbamate impurity was produced with this procedure as compared to prior methods wherein the bis-isopropylamino pyrimidine carbamate impurity required removal by chromatography.

If a formal purification of the mono-isopropylamino pyrimidine 2 step is required, it can be precipitated from THF/ether as the (L)-tartaric acid salt and triturated. A small-scale example follows: (5.09 g, 99.6% yield) L-Tartaric acid (1.42 g) was dissolved in hot THF (45 mL). The hot tartaric acid solution was added to the gum of the isopropylamino-pyrimidine 2 (5.1 g). The mixture was swirled and warmed until homogeneous. The solution changed from pink-purple in color to tan. The solution was concentrated in vacuo to give a tan gum. Ether (~150 mL) was added whereupon oiling was observed. The ether mixture was concentrated in vacuo.

Acetone (~20 mL) and then ether (~200 mL) was added, and the formation of a gummy oil was again observed. The mixture was concentrated for a third time. Methylene chloride (5-10 mL) was added followed by ether (~80 mL). A tan precipitate was observed to form underneath a bright orange-pink supernatant. The mixture was filtered. The precipitate was rinsed with ether (50 mL) and then again with a mixture (~60 mL) of acetone and ether (1:1). The precipitate was dried under vacuum overnight to give a cream colored solid (4.9 g, 76% yield). A small aliquot of the solid tartaric acid salt was dissolved in i-PrOH and EtOH and passed through a small plug of basic alumina to give the free base. The aliquot of free base was analyzed by TLC and LC/MS. The remaining salt was suspended in a mixture of $CH_2Cl_2$ (250 mL) and 1N $NaHCO_3$ (150 mL). With mixing and some bubbling, the solid dissolved and the free base amine was extracted into the organic layer. The aqueous layer was extracted once more with EtOAc (150 mL) and the organic extracts were combined and dried over $MgSO_4$ (~150 g). The dried organic solution was passed through a plug of basic alumina (~100 g) to give a light pink solution that was concentrated in vacuo to give a tan/pink gum (3.28 g, 64% yield from starting nitro-carbamate).

Several other acids were investigated in an attempt to form salts with the mono-isopropylaminopyrimidine carbamate 2. p-Toluenesulfonic acid and methanesulfonic acid gave oils. Solid salts could be formed with HCl and $H_3PO_4$, but tartaric acid appeared to give the most favorable solubility characteristics. The HCl and phosphoric acid salts seemed to dissolve readily in a $CH_2Cl_2$, i-PrOH, and acetone, whereas the tartaric acid salt seemed to be mostly insoluble in $CH_2Cl_2$ and only partially soluble in the other solvents.

Step 2: Preparation of (S)-4-(3-tert-butoxy-2-(2-(diethylamino)-5-(N-isopropylmethylsulfonamido)pyrimidin-4-ylamino)-3-oxopropyl)phenyl pyrrolidine-1-carboxylate (3)

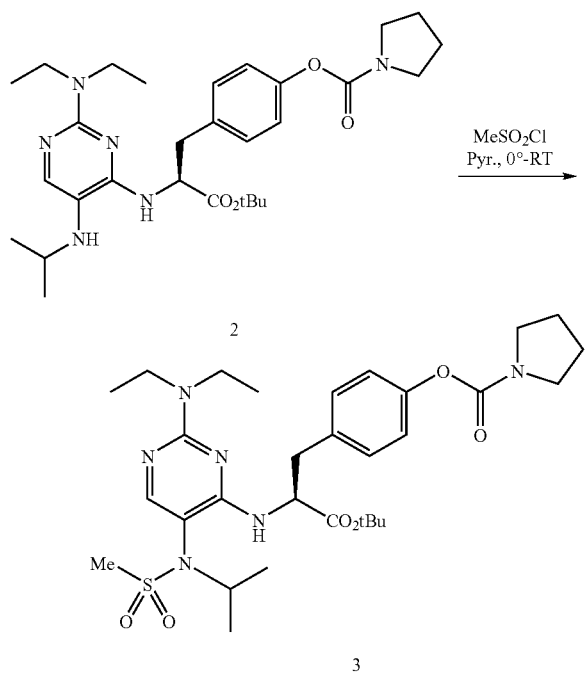

Isopropylaminopyrimidine carbamate 2 from Step 1 (assume 189 mmol) was dissolved in pyridine (680 mL) and the solution was cooled to 0° C. under $N_2$. Methanesulfonyl chloride (44 mL, 3.0 eq.) was added via syringe pump over 20 min. to the cold pyridine solution of the isopropylaminopyrimidine carbamate. The ice bath was removed and the solution was allowed to warm to RT. The solution was allowed to stir for six hours. A small aliquot was removed and a mini-workup was performed (diluted with EtOAc, washed with 5% $KH_2PO_4$, brine, and then dried over $MgSO_4$). Analysis by TLC showed the reaction to be complete and generally clean (only one spot besides a baseline spot from residual pyridine. The bulk reaction solution was concentrated. When 650 mL of distillate had been collected, the blood red oil was diluted with EtOAc (2 L). The organic solution was washed with 5% $KH_2PO_4$ (1 L and 750 mL), 0.2 N citric acid (1 L), and brine (1 L). The organic solution was dried over $MgSO_4$ (150 g). The dried organic solution was filtered through a pad of silica gel (1 L) to give a green-black solution. The flask and silica gel were rinsed with EtOAc (1.5 L) to bring the total volume of organic solution to 3.5 L. The solution was filtered through a pad of basic alumina (300 mL) to give a deep green solution. The solution was concentrated in vacuo. A reddish gum (150 g) was obtained.

The flask was flushed with nitrogen, capped and placed in the refrigerator whereupon a red-brown solid formed. LC/MS indicated acceptable purity, but TLC analysis indicated a bright red baseline spot as well as two to three very faint impurities. The odor of pyridine was still present. The red-brown solid was dissolved in a mixture of $CH_2Cl_2$ (100 mL), THF (200 mL), and ether (800 mL). The solution was filtered/eluted through a pad of silica gel (1 L) and the silica was rinsed with ether (3 L). Most of the colored baseline impurity was retained on the silica gel. The solution was concentrated to give a red oil that dried to a pink foamy solid (100 g) that analyzed to be 94.7% pure by LC/MS. The material was then chromatographed on silica gel (2 L) eluted with $CH_2Cl_2$ (3 L), $CH_2Cl_2$ and ether (1:1; 4 L), ether (4 L), ether:THF (1:1; 4 L), and EtOAc with 5% $Et_3N$ and 2% EtOH (4 L). The $CH_2Cl_2$:ether eluent gave a red oil of mixed fractions (12.4 g; Fraction A) and the ether eluent gave a tan oil (13 g; Fraction B) that was generally pure. The bulk of the material remained on the column and it was realized that the desired product had crystallized on the column. Elution with ether:THF and EtOAc (with 5% $Et_3N$ and 2% EtOH) allowed the product to redissolve and elute in concentrated plug (Fraction C) Fraction A and Fraction B were combined and concentrated together. Fraction C was concentrated separately. Upon concentrating and drying, crystals formed in both fractions. Further investigations found that the solid could be recrystallized from methyl tert-butyl ether (MTBE), cyclohexane, ether-hexane (1:1), MTBE-hexanes, or cyclohexane-hexanes. Combined Fractions A and B and Fraction C were each recrystallized from MTBE-hexanes to give the tert-butyl ester 3 as a white solid (57.75 g total with a purity >99%) and red filtrate/mother liquors. The mother liquors were concentrated to give a red oil (24 g). The mother liquor oil was chromatographed on a Biotage 75 and eluted with 4% THF in $CH_2Cl_2$ (12 L) to give enriched fractions that were then concentrated and re-crystallized to give an additional 14 g of purified tert-butyl ester.

LC/MS by method M2 gave $t_R$=1.97 min. with M/Z=619 for [M+1] for the desired product.

LC/MS by method M15 gave $t_R$=60.0⁹ min. with M/Z=619 for [M+1] for the desired product.

¹H NMR (CDCl₃, 300 MHz)₆, ppm: 0.88 (d, j=6 Hz, 1.4H), 1.04 (d, j=6 Hz, 2H), 1.20 (m, 10H), 1.37 (s, 4.8H), 1.39 (s, 4.8H), 1.93 (AA'BB', 4H), 2.80 (s, 1.7H), 2.9 (s, 1.6H), 3.18 (m, 2.4H), 3.4-3.7 (m overlapping two apparent triplets, 8.3H), 4.40 (sextet, j=6 Hz, 1.1H), 4.8 (sextet, 1H), 5.64 (d, j=6.5 Hz, 0.5H), 5.70 (d, j=6.5 Hz, 0.5H), 7.03 (m, 2H), 7.18 (apparent dd, 2H), 7.80 (d, j=4 Hz, 1H). The ¹H NMR shows rotamers.

It is contemplated that treatment with the methanesulfonyl chloride be done in THF with little or no additional base. If base is used, a base such as triethylamine or diisopropylethylamine should be employed.

Step 3: Preparation of (S)-2-(2-(diethylamino)-5-(N-isopropylmethyl-sulfonamido)pyrimidin-4-ylamino)-3-(4-(pyrrolidine-1-carbonyloxy)phenyl)propanoic acid (4)

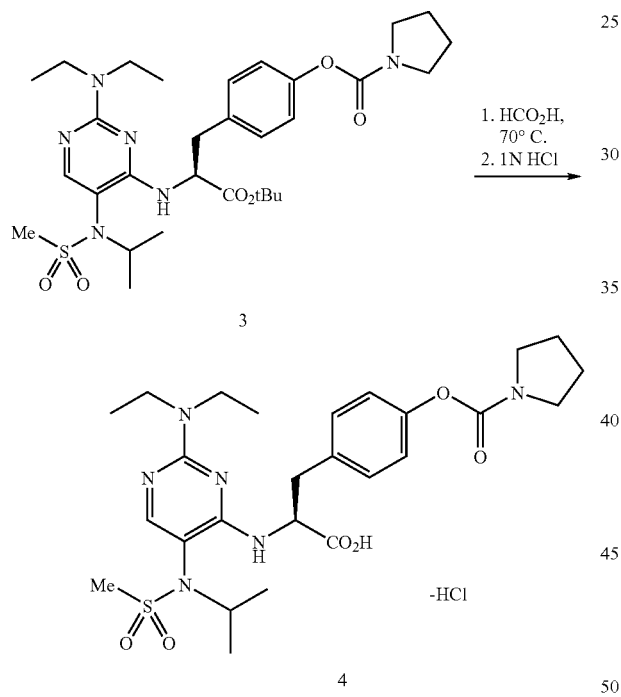

A formic acid (1.5 L) solution of the t-butyl ester from Step 2 (57.75 g, 0.093 mol) was heated to 50° C. overnight and then concentrated in vacuo. Alternatively, the reaction can also be performed at 70° or 80° for 60-90 minutes.

Water (~100 mL) was added to the crude product and the mixture was concentrated to dryness. The residue was dried under high vacuum. The crude product was dissolved and concentrated twice from 1.0N HCl (250 mL and 200 mL). The product was twice dissolved in hot THF and concentrated to dryness to yield a foamy solid. The foamy solid was dried under high vacuum at 650 for two hours. This solid was scraped from the flask and dried in the vacuum oven overnight (60° C., 28 in. Hg) to give the hydrochloride salt of (S)-2-(2-(diethylamino)-5-(N-isopropylmethylsulfonamido)pyrimidin-4-ylamino)-3-(4-(pyrrolidine-1-carbonyloxy)phenyl) propanoic acid-5 (50.9 g; 98.3% pure).

LC/MS by method M15 gave $t_R$=1.96 min. with M/Z=563.

LC/MS by method M2 gave $t_R$=1.43 min. with M/Z=563.

¹H NMR (CD₃OD, 300 MHz) δ, ppm: 0.80 (d, j=6 Hz, 1.4H), 1.02 (d, j=6 Hz, 1.6H), 1.23 (m, 9.2H), 1.80-2.0 (AA'BB'+m, 5.2H), 2.99 (d, 3.2H), 3.2-3.45 (m, 4.5H), 3.45-3.8 (m, 7.6H), 4.40 (sextet, 1H), 4.90 (m, 3H), 7.00 (d, 2H), 7.23 (d, 2H), 7.60 (d, 0.25H), 7.75 (d, 1H), 7.83 (d, 0.25H).

¹³C NMR (CD₃OD, 75 MHz) δ, ppm: 6.5, 14.7, 14.8, 15.4, 15.5, 19.4, 20.0, 20.2, 29.91, 30.44, 33.95, 34.15, 41.03, 41.08, (41.71, 41.99, 42.28, 42.6, 42.8, 43.1—solvent peaks), 47.21, 47.36, 50.01, 50.42, 62.43, 102.11, 102.23, 116.78, 124.9, 125.19, 128.54, 129.01, 138.49, 139.02, 145.53, 145.60, 145.78, 148.68, 156.77, 156.86, 166.91, 167.07.

Example 2

Preparation of (S)-2-(2-(diethylamino)-5-(N-ethylmethylsulfonamido)pyrimidin-4-ylamino)-3-(4-(pyrrolidine-1-carbonyloxy)phenyl)propanoic acid (7)

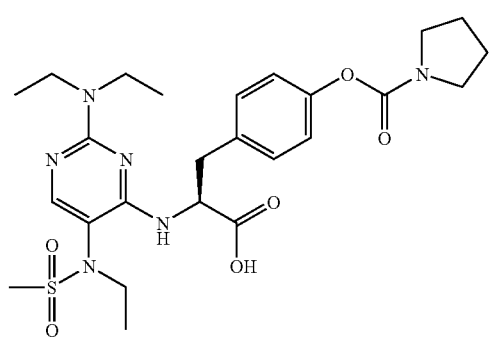

Step 1: One-pot reduction/reductive ethylation of (S)-4-(3-tert-butoxy-2-(2-(diethylamino)-5-nitropyrimidin-4-ylamino)-3-oxopropyl)phenyl pyrrolidine-1-carboxylate (6)

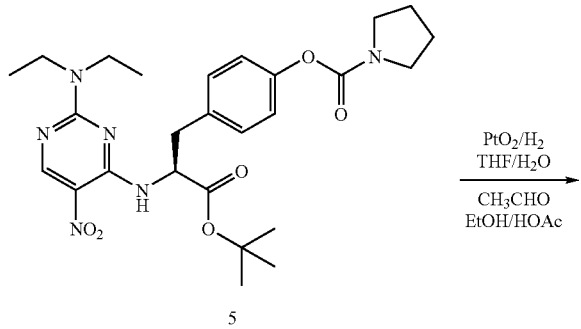

-continued

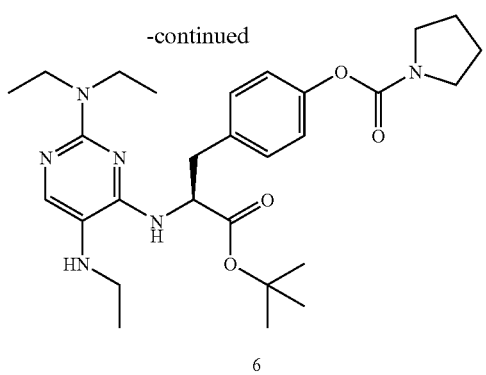

6

Nitro-carbamate (compound 5, 10.8 g, 20 mmol) was slurried in THF (35 mL) and water (1 mL, 3 vol %) was added. The solution was stirred, Adams catalyst (0.360 g, 6 mole %) was added and the solution was de-oxygenated by three cycles of evacuation (50 mm Hg) and refilling with dry nitrogen (10 psi). Finally, the reaction vessel was pressurized with hydrogen (60 psi) and reaction mixture was vigorously stirred for 90 min. If necessary or desired, progress of the hydrogenation reaction can be monitored by TLC (silica gel, eluting with dichloromethane:methanol (95:5)). $R_f$ of nitrocarbamate is 0.95, primary amine=0.16.

The hydrogen was replaced by dry nitrogen (three cycles of evacuation and refilling with nitrogen). The ethanol (25 mL), acetic acid (0.3 mL) and acetaldehyde (1.2 mL, 21 mmol, 1.05 eq) were added, vessel was partially evacuated at low pressures (ca. 150 mm Hg) in order to minimize loss of the volatile acetaldehyde, refilled with nitrogen (10 psi) and reaction mixture was stirred vigorously for 50 min. At the end of this time, nitrogen was replaced by hydrogen (60 psi) by partial evacuation and re-pressurizing with hydrogen two times. The mixture was stirred for another 45 min. Progress of reductive amination may be monitored by TLC (silica gel, eluting with dichloromethane:methanol (95:5). $R_f$ of primary amine=0.16, secondary amine=0.32 and tertiary amine=0.43. At the end of process, hydrogen was flushed out by three cycles of evacuation and refilling with nitrogen, the catalyst was filtered off on a bed of Celite using methanol to rinse, the filtrates were stripped to dryness to give amber oil (11.9 g). The product is sensitive to oxygen, resulting in considerable darkening and appearance of low $R_f$ material in TLC. All handling should be done with appropriate precautions.

The reaction product was purified by flash chromatography using dichloro-methane:methanol mixture (97:3), containing 0.3% of ammonium hydroxide. Fractions containing N-ethyl product were combined to give 7.9 g of compound 6 as an amber oil (98.5% pure; 73% yield). The purity of the crude product appears to be adequate for many purposes, especially if product of the subsequent anticipated reactions is known to be crystalline.

$^1$H-NMR, CDCl$_3$, (δ): 7.60 (s, 1H), 7.17 (d, J=8.4 Hz, 2H), 7.05 (d, J=8.4 Hz, 2H), 5.75 (d, J=7.5 Hz, 1H), 4.84 (q, J=6.6 Hz, 1H), 3.64-3.46 (m, 8H), 3.19 (d, J=6.3 Hz, 2H), 2.86 (q, J=7.2 Hz, 2H), 1.94 (m, 4H), 1.39 (s, 9H), 1.20-1.11 (m, 9H).

$^{13}$C-NMR, CDCl$_3$, (δ): 171.7, 157.7, 157.5, 153.1, 150.3, 145.8, 133.7, 130.2, 121.5, 117.4, 81.8, 54.7, 46.4, 46.3, 42.4, 41.7, 37.4, 28.0, 25.8, 24.9, 15.5, 13.5.

MS (m/z): 527.3 [M+1].

Steps 2 and 3: (S)-2-(2-(diethylamino)-5-(N-ethylmethylsulfonamido)-pyrimidin-4-ylamino)-3-(4-(pyrrolidine-1-carbonyloxy)phenyl)propanoic acid 7

Following the procedures of Steps 2 and 3 of Example 1, compound 6 was converted to the corresponding (S)-2-(2-(diethylamino)-5-(N-ethylmethylsulfonamido)pyrimidin-4-ylamino)-3-(4-(pyrrolidine-1-carbonyloxy)phenyl)propanoic acid 7 which was characterized as follows:

$^1$H-NMR, CDCl$_3$, (δ): 8.17 (s, 1H), 7.77 (s, 1H), 7.26-7.23 (m, 2H), 7.00-6.98 (d, 2H), 4.85-4.82 (m, 1H), 3.58-3.51 (m, 6H), 3.43-3.39 (m, 3H), 2.96-2.84 (m, 3H), 2.01-1.91 (m, 4H), 1.29-0.97 (m, 9H);

$^{13}$C-NMR, CDCl$_3$, (δ): 175.6, 165.7, 157.2, 155.2, 152.0, 151.8, 151.7, 151.3, 136.0, 135.9, 131.5, 123.0, 110.5, 56.7, 43.8, 39.4, 39.2, 37.4, 26.7, 25.8, 14.4, 13.3; and

MS: M(+H) 549

Example 3

Preparation of (S)-2-(5-(N-cyclopentylmethylsulfonamido)-2-(diethylamino)pyrimidin-4-ylamino)-3-(4-(pyrrolidine-1-carbonyloxy)phenyl)propanoic acid (8)

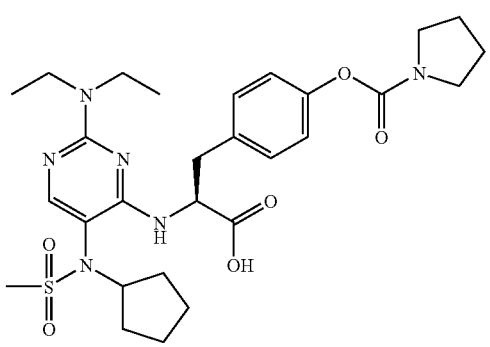

8

Following the procedures of Example 1 and employing cyclopentanone in place of acetone (Example 1) or acetaldehyde (Example 2), (S)-2-(5-(N-cyclopentylmethylsulfonamido)-2-(diethylamino)pyrimidin-4-ylamino)-3-(4-(pyrrolidine-1-carbonyloxy)phenyl)propanoic acid 8 was prepared and characterized as follows:

$^1$H-NMR, CDCl$_3$, (δ): 7.74-7.71 (d, 1H), 7.28-7.24 (m, 2H), 7.04-7.00 (m, 2H), 5.00-4.95 (m, 1H), 4.37-4.27 (m, 1H), 3.60-3.37 (m, 9H), 3.00-2.97 (d, 3H), 2.03-1.78 (m, 6H), 1.67-1.40 (m, 6H), 1.31-1.23 (m, 6H);

$^{13}$C-NMR, CDCl$_3$, (δ): 173.6, 173.4, 163.1, 155.1, 152.4, 152.0, 145.3, 144.7, 135.5, 135.1, 131.6, 131.4, 123.2, 109.6, 109.4, 62.5, 62.3, 56.7, 56.5, 48.1, 40.3, 40.1, 36.8, 36.4, 31.2, 30.5, 26.7, 25.8, 23.2, 23.1, 12.7; and

MS: M(+H) 589.

Example 4
Preparation of (S)-2-(2-(diethylamino)-5-(N-(prop-2-ynyl)methylsulfonamido)pyrimidin-4-ylamino)-3-(4-(pyrrolidine-1-carbonyloxy)phenyl)propanoic acid (13)
The synthetic protocol employed in Example 4 is summarized in Scheme 6 illustrated below:
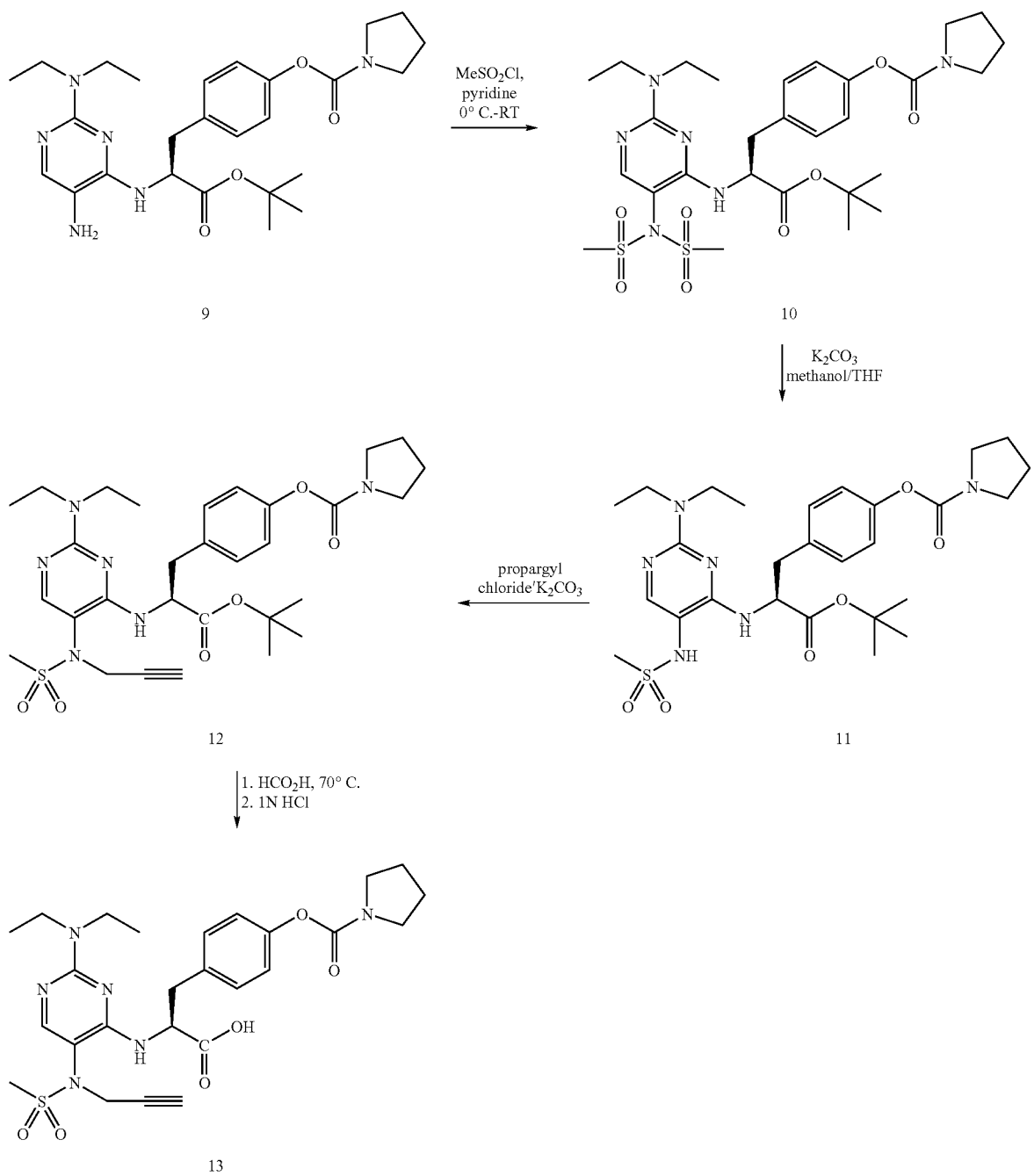

Step 1: (S)-4-(3-tert-butoxy-2-(2-(diethylamino)-5-(N-(methylsulfonyl)-methylsulfonamido)pyrimidin-4-ylamino)-3-oxopropyl)phenyl pyrrolidine-1-carboxylate (10)

Aminopyrimidine (2.0 g, 4.0 mmol—compound 9) (prepared by reduction of compound 1) was dissolved in dichloromethane (10 mL). THF (10 mL) and triethylamine (2.8 mL, 20 mmol) were added and the reaction cooled in an ice bath. Methanesulfonyl chloride (1.1 mL, 14 mmol) was added and the reaction warmed to room temperature over 18 hours. The reaction mixture was concentrated in vacuo and the residue taken up in ethyl acetate. The solution was washed with 0.2 N citric acid, water, sat. NaHCO$_3$, and brine. The organic layer was dried over Na$_2$SO$_4$, filtered, and concentrated in vacuo to yield crude product as a brown foam. The residue was purified by flash chromatography (2:3 ethyl acetate/hexanes) to yield 2.2 g (73%) of the di-sulfonylated material as a yellow foam (compound 10).

Step 2: (S)-4-(3-tert-butoxy-2-(2-(diethylamino)-5-(methylsulfonamido)-pyrimidin-4-ylamino)-3-oxopropyl)phenyl pyrrolidine-1-carboxylate (11)

Compound 10 (2.2 g, 3.4 mmol) was dissolved in methanol (5 mL) and THF (5 mL). 1.0 M K$_2$CO$_3$ (10 mL) was added and the reaction mixture was heated at 40° C. for 96 hours. The reaction mixture was acidified to pH 3 with 2N HCl and extracted with ethyl acetate. The organic layer was washed with brine, dried over Na$_2$SO$_4$, filtered, and concentrated in vacuo to yield 1.68 g (86%) product as a beige foam, compound 11. The crude material was used without purification.

Step 3: (S)-4-(3-tert-butoxy-2-(2-(diethylamino)-5-(N-(prop-2-ynyl)methyl-sulfonamido)pyrimidin-4-ylamino)-3-oxopropyl)phenyl pyrrolidine-1-carboxylate (12)

Compound 11 (0.20 g, 0.35 mmol), K$_2$CO$_3$ (0.073 g, 0.53 mmol), and acetone (3 mL) were placed in a sealed tube and stirred at room temperature for one hour. Propargyl chloride (0.26 mL, 3.5 mmol) was added and the reaction was sealed and heated at reflux for 48 hours. The reaction mixture was concentrated in vacuo and the residue taken up in ethyl acetate. The solution was washed with water and brine. The organic layer was dried over Na$_2$SO$_4$, filtered, and concentrated in vacuo to yield crude product as an orange film. The residue was purified by flash chromatography (1:1 ethyl acetate/hexanes) to yield 0.11 g (51%) of compound 12 as a transparent film.

MS (m/z) 615, (M+H)$^+$.

Step 4: (S)-2-(2-(diethylamino)-5-(N-(prop-2-ynyl)methylsulfonamido)-pyrimidin-4-ylamino)-3-(4-(pyrrolidine-1-carbonyloxy)phenyl)propanoic acid (13)

Formic acid (2 mL) was added to t-butyl ester (100 mg) and stirred at 40° C. over night. The formic acid was removed under reduced pressure to yield compound 13 in quantitative yield and characterized as follows:

$^1$H-NMR, CDCl$_3$, (δ): 8.13 (s, 1H), 7.97 (s, 1H), 7.26-7.24 (d, 2H), 7.02-6.99 (d, 2H), 4.59-4.44 (m, 1H), 4.04-3.79 (m, 1H), 3.64-3.53 (m, 6H), 3.45-3.39 (t, 3H), 3.08-2.84 (m, 4H), 2.84-1.89 (m, 4H) 1.22-1.17 (t, 6H);

$^{13}$C-NMR, CDCl$_3$, (δ): 165.3, 155.3, 151.8, 136.1, 131.5, 123.0, 76.1, 76.0, 56.8, 49.9, 48.1, 43.8, 41.2, 40.2, 37.4, 26.7, 25.9, 13.3; and

MS: M(+H) 559.

Example 5

Preparation of (S)-2-(2-(diethylamino)-5-(N-methylmethylsulfonamido)-pyrimidin-4-ylamino)-3-(4-(pyrrolidine-1-carbonyloxy)phenyl)propanoic acid (14)

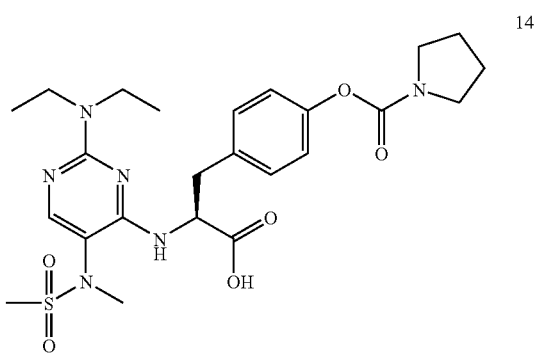

14

Following the procedures of Example 4 and employing dimethylsulfate in place of propargyl chloride, the title compound was prepared and was characterized as follows:

$^1$H-NMR, CDCl$_3$, (δ): 8.14 (s, 1H), 7.83 (s, 1H), 7.26-7.23 (d, 2H), 7.01-6.98 (d, 2H), 4.84-4.81 (m, 1H), 3.60-3.53 (m, 6H), 3.43-3.38 (m, 3H), 3.09 (s, 3H), 2.94 (s, 3H), 2.00-1.91 (m, 4H), 1.22-1.18 (t, 6H);

$^{13}$C-NMR, CDCl$_3$, (δ): 175.5, 165.4, 160.7, 156.3, 155.3, 151.8, 149.1, 136.0, 131.6, 123.0, 113.4, 56.9, 43.9, 38.8, 38.1, 37.4, 26.7, 25.8, 13.2; and

MS: M(+H) 535.

Example A

α4β1 Integrin Adhesion Assay

Jurkat™ Cell Adhesion to Human Plasma Fibronectin Procedure 96 well plates (Costar 3590 EIA plates) were coated with human fibronectin (Gibco/BRL, cat #33016-023) at a concentration of 10 μg/mL overnight at 4° C. The plates were then blocked with a solution of bovine serum albumin (BSA; 0.3%) in saline. Jurkat™ cells (maintained in log phase growth) were labeled with calcein AM according to the manufacturer's instructions, and suspended at a concentration of 2×10$^6$ cells/mL in Hepes/Saline/BSA. The cells were then exposed to test and control compounds for 30 minutes at room temperature before transfer to individual wells of the fibronectin coated plate. Adhesion was allowed to occur for 35 minutes at 37° C. The wells were then washed by gentle aspiration and pipetting with fresh saline. Fluorescence associated with the remaining adherent cells was quantified using a fluorescence plate reader at EX 485/EM 530.

Cell cultures were prepared by first splitting the stationary phase Jurkat™ cells at 1:10 on day one and 1:2 on day two to perform assay on day 3. The cells split 1:10 on day one were split 1:4 on day 3 for a day 4 assay.

The assay plates were prepared by first making a working solution of Gibco/BRL Human Fibronectin (cat #33016-023) in PBS++, at 10 µg/mL.

A Costar 3590 EIA plate was then coated with 50 µL/well for 2 hours at room temperature (though it can also be left overnight at 4° C.). Finally the plate was aspirated and blocked with Hepes/Saline Buffer, 100 µL/well, for 1 hour at rt followed by washing three times with 150 L of PBS++.

Compound dilutions were accomplished by preparing 1:3 serial dilutions of compounds as follows. For each plate (4 compounds/plate) 600 µL were added to 4 Bio-Rad Titertubes in a Titertube rack. Enough compound was added to each appropriate tube to give a 2× concentration using methods well known in the art. Using Falcon Flexiplates, 100 µL of Hepes/Saline buffer or human serum were added to rows B through G. A multi-channel pipetter set to 180 µL was used to with four tips spaced evenly on the pipetter. Each set of four tubes was mixed 5 times and 180 µL of 2× compound was transferred to the first column of each compound dilution in Row B, leaving Row A empty. 180 µL were added to the other wells in Row A. Serial dilutions were performed down the plate by transferring 50 µL to the next dilution and mixing 5 times, changing tips each time after mixing. Dilutions were stopped at Row F. Row G had no compound present.

A 20 µg/ml solution in HEPES/saline buffer or human serum, of 21/6 antibody was the positive control and was set aside in a reagent trough to add to cell suspension plate.

The cell staining was accomplished by first harvesting the log-phase Jurkat™ cells by centrifugation in 50 mL tubes (1100 rpm for 5 minutes). The cells were resuspended in 50 mL PBS++, spun, and resuspended in 20 mL PBS++. The cells were stained by adding 20 µL of Calcein AM for 30 minutes at RT. The volume was brought to 50 mL with HEPES/saline buffer and the cells were counted, spun, and resuspended to $2 \times 10^6$ cells/mL in HEPES/saline buffer or human serum.

The compounds were incubated using the following procedure. In a new flexiplate, 65 µL of stained cells were added to Rows B through H. Then 65 µL of 2× compounds were added to the appropriate rows following the plate setup and mixed 3×. 65 µL of 2X-21/6 antibody were added to Row H and mixed 3 times. Finally the plate was incubated at room temperature for 30 minutes.

Fibronectin adhesion was measured using a fluorescent plate reader at EX 485/EM 530 after the following work up procedure. After incubation, the cells were mixed 3× and 100 µL were transferred to the fibronectin coated plates and incubated at 37° C. for about 35 minutes. Each plate was washed, row by row, by gently pipetting 100 µL of RT PBS++ down the sides of the wells and turning the plate 90 degrees to aspirate. This procedure was repeated for a total of 3 washes. Each well was filled with 100 µL after washing by pipetting down the side of the well.

An $IC_{50}$ value was calculated for each compound, both in the presence of the human serum and in the absence of human serum. $IC_{50}$ is concentration at which the growth or activity is inhibited by 50%. The compounds disclosed herein were all found to have an $IC_{50}$ of less than 0.1 µM when tested according to the fibronectin assay.

Example B

In vitro Saturation Assay For Determining Binding of Candidate Compounds to α4β1

Log-growth Jurkat™ cells were washed and resuspended in normal animal plasma containing 20 µg/mL of the 15/7 antibody (Yednock, et al., J. Biol. Chem., (1995) 270(48): 28740).

The Jurkat™ cells were diluted two-fold into either normal plasma samples containing known candidate compound amounts in various concentrations ranging from 66 µM to 0.01 µM, using a standard 12 point serial dilution for a standard curve, or into plasma samples obtained from the peripheral blood of candidate compound-treated animals.

Cells were then incubated for 30 minutes at room temperature, washed twice with phosphate-buffered saline ("PBS") containing 2% fetal bovine serum and 1 mM each of calcium chloride and magnesium chloride (assay medium) to remove unbound 15/7 antibody.

The cells were then exposed to phycoerythrin-conjugated goat F(ab')2 anti-mouse IgG Fc (Immunotech, Westbrook, Me.), which had been adsorbed for any non-specific cross-reactivity by co-incubation with 5% serum from the animal species being studied, at 1:200 and incubated in the dark at 4° C. for 30 minutes.

Cells were washed twice with assay medium and resuspended in the same. They were then analyzed with a standard fluorescence activated cell sorter ("FACS") analysis as described in Yednock et al., J. Biol. Chem., 1995, 270:28740.

The data was then graphed as fluorescence versus dose, e.g., in a normal dose-response fashion. The dose levels that result in the upper plateau of the curve represent the levels needed to obtain efficacy in an in vivo model.

The results of the α4-dependent in vitro potency assay indicate that certain compounds of this invention when tested in this assay showed inhibition of α4β1 integrin at an $EC_{50}$ of less than 20 µg/mL.

Example C

In Vitro Assay For Determining Binding of Compounds to VLA-4

An in vitro assay was used to assess binding of candidate compounds to $\alpha_4\beta_1$ integrin. Compounds which bind in this assay can be used to assess VCAM-1 levels in biological samples by conventional assays (e.g., competitive assays). This assay is sensitive to $IC_{50}$ values as low as about 1 µM.

The activity of $\alpha_4\beta_1$ integrin was measured by the interaction of soluble VCAM-1 with Jurkat™ cells (e.g., American Type Culture Collection Nos. TIB 152, TIB 153, and CRL 8163), a human T-cell line which expresses high levels of $\alpha_4\beta_1$ integrin. VCAM-1 interacts with the cell surface in an $\alpha_4\beta_1$ integrin-dependent fashion (Yednock, et al. J. Biol. Chem., 1995, 270:28740).

Recombinant soluble VCAM-1 was expressed as a chimeric fusion protein containing the seven extracellular domains of VCAM-1 on the N-terminus and the human $IgG_1$ heavy chain constant region on the C-terminus. The VCAM-1 fusion protein was made and purified by the manner described by Yednock, supra.

Jurkat™ cells were grown in RPMI 1640 supplemented with 10% fetal bovine serum, penicillin, streptomycin and glutamine as described by Yednock, supra.

Jurkat™ cells were incubated with 1.5 mM MnCl and 5 μg/mL 15/7 antibody for 30 minutes on ice. $Mn^{+2}$ activates the receptor to enhance ligand binding, and 15/7 is a monoclonal antibody that recognizes an activated/ligand occupied conformation of $\alpha_4\beta_1$ integrin and locks the molecule into this conformation thereby stabilizing the VCAM-1/$\alpha_4\beta_1$ integrin interaction. Yednock, et al., supra. Antibodies similar to the 15/7 antibody have been prepared by other investigators (Luque, et al, 1996, J. Biol. Chem. 271:11067) and may be used in this assay.

Cells were then incubated for 30 minutes at room temperature with candidate compounds, in various concentrations ranging from 66 μM to 0.01 μM using a standard 5-point serial dilution. 15 μL soluble recombinant VCAM-1 fusion protein was then added to Jurkat™ cells and incubated for 30 minutes on ice. Yednock et al., supra.

Cells were then washed two times and resuspended in PE-conjugated goat F(ab')$_2$ anti-mouse IgG Fc (Immunotech, Westbrook, Me.) at 1:200 and incubated on ice, in the dark, for 30 minutes. Cells were washed twice and analyzed with a standard fluorescence activated cell sorter ("FACS") analysis as described in Yednock, et al., supra.

Compounds having an $IC_{50}$ of less than about 15 μM possess binding affinity to $\alpha_4\beta_1$.

When tested in this assay, the compounds prepared in the above examples has or is expected to have an $IC_{50}$ of 15 μM or less (or is expected to be active in vivo). A certain compound of this assay had an $IC_{50}$ of less than 5 μM.

Example D

Cassette Dosing and Serum Analysis for Determination of Bioavailability

The oral bioavailability was screened by dosing rats with a cassette, i.e. mixture of 6 compounds per dosing solution. The cassette includes 5 test articles and a standard compound, for a total dose of 10 mg/kg. Each compound/test article was converted to the sodium salt with equimolar 1 N NaOH and dissolved in water at 2 mg/mL. The cassette was prepared by mixing equal volumes of each of the six solutions. The cassette dosing solution was mixed well and then the pH was adjusted to 7.5-9. The dosing solution was prepared the day before the study and is stirred overnight at room temperature.

Male Sprague Dawley (SD) rats from Charles River Laboratories, 6-8 weeks old, were used in this screen. Rats were quarantined for at least one day and had continuous access to food and water. On the night before the administration of the cassette, the rats were fasted for approximately 16 h.

Four SD rats were assigned in each cassette. A single dose of the dosing solution was administered orally to each rat. The dosing volume (5 mL/kg) and time were recorded and rats were fed 2 h after dosing.

Blood samples were collected via cardiac puncture at the following time points: 4 h, 8 h and 12 h. Immediately prior to blood collection, rats were anesthetized with $CO_2$ gas within 10-20 seconds. After the 12-hour samples were collected, the rats were euthanized via $CO_2$ asphyxiation followed by cervical dislocation.

Blood samples were kept in heparinized microtainer tubes under subambient temperature (4° C.) before they are processed. Blood samples were centrifuged (10,000 rpm for 5 minutes) and plasma samples were removed and stored in a −20° C. freezer until analyzed for drug levels. Drug levels in the plasma were analyzed using the following protocol for direct plasma precipitation.

The in vivo plasma samples were prepared in a 1.5 mL 96-well plate, by adding, in order, 100 μL of the test plasma, 150 μl of methanol, followed by vortexing for 10-20 seconds. 150 μL of 0.05 ng/μL of an Internal Standard in acetonitrile were added and vortexed for 30 seconds.

The standard curve samples were prepared in a 1.5 mL 96-well plate, by adding, in order, 100 μL of control mouse plasma, followed by 150 μL of methanol and vortexing for 10-20 seconds. 150 μL of 0.05 ng/μL of an Internal Standard in acetonitrile were added and vortexed for 30 seconds. The samples were spiked with 0-200 ng (10 concentrations) of the compound of interest in 50% methanol to obtain a standard curve range of 0.5 ng/mL to 2,000 ng/mL. Again, the sample is vortexed for 30 seconds.

The samples were then spun for 20-30 minutes at 3,000 rpm in an Eppendorf microfuge before 80-90% of supernatant is transferred into a clean 96-well plate. The organic solvent was then evaporated until the samples are dry (under $N_2$ at 40° C./30-60 min. (ZymarkTurbovap)).

The residue was then dissolved in 200-600 L mobile phase (50% $CH_3OH$/0.1% TFA). LC/MS/MS was then run using a PE-Sciex API-3000 triple quadrupole mass spectrometer (SN0749707), Perkin-Elmer, Series200auto-sampler, and Shimadzu 10A pump. Acquisition was done with PE-Sciex Analyst (v 1.1) and data analysis and quantification were accomplished using PE-Sciex Analyst (v 1.1). A 5-50 μl sample volume was injected onto a reverse phase ThermoHypersil DASH-18 column (Keystone 2.0×20 mm, 5 μm, PN: 8823025-701) using a mobile phase of 25% $CH_3OH$, 0.1% TFA-100% $CH_3OH$, 0.1% TFA. The run time was about 8 minutes at a flow rate of about 300 μL/minutes.

The Area Under the Curve (AUC) was calculated using the linear trapezoidal rule from t=0 to the last plasma concentration sampling time tx (see Handbook of Basic Pharmacokinetics, Wolfgang A. Ritschel and Gregory L. Kearns, 5th ed, 1999).

$$AUC^{0-tx} = \Sigma^{0-n}((C_n + C_{n+1})/2) \cdot (t_{n+1} - t_n) \text{ [in (μg/mL)h]}$$

In the case of the cassette dosing paradigm, samples at 4, 8 and 12 h post extravascular dosing, the AUC was calculated from t=0 to t=12 h.

Each of the compounds in Examples 1-5 above when tested in this assay provided for an AUC of at least 5 μgh/mL when normalized for administration at a 10 mg/kg dose.

Example E

Asthma Models

E1

Inflammatory conditions mediated by $\alpha_4\beta_1$ integrin include, for example, eosinophil influx, airway hyper-responsiveness and occlusion that occurs with chronic asthma. The following describes animal models of asthma that are used to study the in vivo effects of the compounds of this invention for use in treating asthma.

Rat Asthma Model

E2

Following the procedures described by Chapman, et al., Am J. Resp. Crit. Care Med., 153-4, A219 (1996) and Chapman, et al., Am. J. Resp. Crit. Care Med. 155:4, A881 (1997), both of which are incorporated by reference in their entirety. Ovalbumin (OA; 10 μg/mL) is mixed with aluminum hydroxide (10 mg/mL) and injected (i.p.) in Brown Norway rats on day 0. Injections of OA, together with adjuvant, are repeated on days 7 and 14. On day 21, sensitized animals are restrained in plastic tubes and exposed (60 minutes) to an aerosol of OA (10 mg/kg) in a nose-only exposure system. Animals are sacrificed 72 hours later with pentobarbital (250 mg/kg, i.p.). The lungs are lavaged via a tracheal cannula using 3 aliquots (4 mL) of Hank's solution (HBSS×10, 100 ml; EDTA 100 mM, 100 mL; HEPES 1 M, 25 mL; made up to 1 L with $H_2O$); recovered cells are pooled and the total volume of recovered fluid adjusted to 12 mL by addition of Hank's solution. Total cells are counted (Sysmex microcell counter F-500, TOA Medical Electronics Otd., Japan) and smears are made by diluting recovered fluid (to approximately 106 cells/mL) and pipetting an aliquot (100 μl) into a centrifuge (Cytospin, Shandon, U.K.). Smears are air dried, fixed using a solution of fast green in methanol (2 mg/mL) for 5 seconds and stained with eosin G (5 seconds) and thiazine (5 seconds) (Diff-Quick, Browne Ltd. U.K.) in order to differentiate eosinophils, neutrophils, macrophages and lymphocytes. A total of 500 cells per smear are counted by light microscopy under oil immersion (×100). Compounds of this invention can be formulated into a 0.5% carboxymethylcellulose and 2% Tween 80 suspension and administered orally to rats which had been sensitized to the allergen, ovalbumin. Compounds which inhibited allergen-induced leucocyte accumulation in the airways of actively sensitized Brown Norway rats are considered to be active in this model.

Mouse Asthma Model

E3

Compounds are also evaluated in a mouse model of acute pulmonary inflammation following the procedures described by, Kung, et al., Am J. Respir. Cell Mol. Biol., 13:360-365, (1995) and Schneider, et al., (1999). Am J. Respir. Cell Mol. Biol. 20:448-457, (1999), which are each incorporated by reference in their entirety. Female Black/6 mice (8-12 weeks of age) are sensitized on day 1 by an intraperitoneal injection of 0.2 mL ova/alum mixture containing 20 μg of ova (Grade 4, Sigma) and 2 mg inject Alum (Pierce). A booster injection is administered on day 14. Mice are challenged on days 28 and 29 with aerosolized 1% ova (in 0.9% saline) for 20 minutes. Mice are euthanized and bronchaveolar lavage samples (3 mL) are collected on day 30, 48 hours post first challenge. Eosinophils are quantified by a FACS/FITC staining method. Compounds of this invention are formulated into a 0.5% carboxymethylcellulose and 2% Tween 80 suspension and administered orally to mice which had been sensitized to the allergen, ovalbumin. Compounds which inhibited allergen-induced leucocyte accumulation in the airways of actively sensitized C57BL/6 mice are considered to be active in this model.

Sheep Asthma Model

E4

This model employs the procedures described by Abraham, et al., J. Clin, Invest, 93:776-787 (1994) and Abraham, et al., Am J. Respir. Crit. Care Med., 156:696-703 (1997), both of which are incorporated by reference in their entirety. Compounds of this invention are evaluated by intravenous (saline aqueous solution), oral (2% Tween 80, 0.5% carboxymethylcellulose), and aerosol administration to sheep which are hypersensitive to *Ascaris suum* antigen. Compounds which decrease the early antigen-induced bronchial response and/or block the late-phase airway response, e.g. have a protective effect against antigen-induced late responses and airway hyper-responsiveness ("AHR"), are considered to be active in this model.

Allergic sheep which are shown to develop both early and late bronchial responses to inhaled *Ascaris suum* antigen are used to study the airway effects of the candidate compounds. Following topical anesthesia of the nasal passages with 2% lidocaine, a balloon catheter is advanced through one nostril into the lower esophagus. The animals are then incubated with a cuffed endotracheal tube through the other nostril with a flexible fiberoptic bronchoscope as a guide.

Pleural pressure is estimated according to Abraham (1994). Aerosols (see formulation below) are generated using a disposable medical nebulizer that provided an aerosol with a mass median aerodynamic diameter of 3.2 μm as determined with an Andersen cascade impactor. The nebulizer is connected to a dosimeter system consisting of a solenoid valve and a source of compressed air (20 psi). The output of the nebulizer is directed into a plastic T-piece, one end of which is connected to the inspiratory port of a piston respirator. The solenoid valve is activated for 1 second at the beginning of the inspiratory cycle of the respirator. Aerosols are delivered at VT of 500 mL and a rate of 20 breaths/minute. A 0.5% sodium bicarbonate solution only is used as a control.

To assess bronchial responsiveness, cumulative concentration-response curves to carbachol is generated according to Abraham (1994). Bronchial biopsies are taken prior to and following the initiation of treatment and 24 hours after antigen challenge. Bronchial biopsies are preformed according to Abraham (1994).

An in vitro adhesion study of alveolar macrophages can also be performed according to Abraham (1994), and a percentage of adherent cells can be calculated.

Aerosol Formulation

A solution of compound n 0.5% sodium bicarbonate/saline (w/v) at a concentration of 30.0 mg/mL is prepared using the following procedure:

A. Preparation of 0.5% Sodium Bicarbonate/Saline Stock Solution: 100.0 mL

| Ingredient | Gram/100.0 mL | Final Concentration |
|---|---|---|
| Sodium Bicarbonate | 0.5 g | 0.5% |
| Saline | q.s. ad 100.0 mL | q.s. ad 100% |

Procedure:
1. Add 0.5 g sodium bicarbonate into a 100 mL volumetric flask.
2. Add approximately 90.0 mL saline and sonicate until dissolved.
3. Q.S. to 100.0 mL with saline and mix thoroughly.

B. Preparation of 30.0 mg/mL Compound: 10.0 mL

| Ingredient | Gram/10.0 mL | Final Concentration |
|---|---|---|
| Compound | 0.300 g | 30.0 mg/mL |
| 0.5% Sodium Bicarbonate/Saline Stock Solution | q.s. ad 10.0 mL | q.s ad 100% |

Procedure:
1. Add 0.300 g of the compound into a 10.0 mL volumetric flask.
2. Add approximately 9.7 mL of 0.5% sodium bicarbonate/saline stock solution.
3. Sonicate until the compound is completely dissolved.
4. Q.S. to 10.0 mL with 0.5% sodium bicarbonate/saline stock solution and mix thoroughly.

Example F

Adjuvant-Induced Arthritis in Rats

Adjuvant induced arthritis ("AIA") is an animal model useful in the study of rheumatoid arthritis ("RA"), which is induced by injecting *M. tuberculosis* in the base of the tail of Lewis rats. Between 10 and 15 days following injection, animals develop a severe, progressive arthritis.

Generally, compounds are tested for their ability to alter hind paw swelling and bone damage resulting from adjuvant induced edema in rats. To quantitate the inhibition of hind paw swelling resulting from AIA, two phases of inflammation have been defined: (1) the primary and secondary injected hind paw, and (2) the secondary uninjected hind paw, which generally begins developing about eleven days from the induction of inflammation in the injected paw. Reduction of the latter type of inflammation is an indication of immunosuppressive activity. Cf. Chang, Arth. Rheum., 20, 1135-1141 (1977).

Using an animal model of RA, such as AIA, enables one to study the cellular events involved in the early stages of the disease. CD44 expression on macrophages and lymphocytes is up regulated during the early development of adjuvant arthritis, whereas LFA 1 expression is up regulated later in the development of the disease. Understanding the interactions between adhesion molecules and endothelium at the earliest stages of adjuvant arthritis could lead to significant advances in the methods used in the treatment of RA.

Example G

Collagen Induced Arthritis in Rats

Purpose: To determine the efficacy of a representative compound of the invention ("Compound A") administered by po bid dosing (Days (-1)-20) for inhibition of the inflammation, cartilage destruction and bone resorption that occurs in developing type TI collagen arthritis in rats.

Animals: 54 Female Lewis rats (Harlan), weighing 125-150 g on arrival. (inject 50 with collagen to get 50 responders on days 10, 11, 12 for 6 groups of 10). The animals (10/group for arthritis, 4/group for normal control), housed 4-5/cage, were acclimated for 4-8 days. The animals were dosed at po3 mg/kg bid, po10 mg/kg bid, and po30 mg/kg bid.

Materials: Agents or drugs in vehicle, Type II collagen, Freund's incomplete adjuvant, methotrexate (Sigma), Compound A General Study Design Dosing was initiated on day minus 1.

The acclimated animals were anesthetized with isoflurane and given collagen injections (D0). On day 6 they were anesthetized again for the second collagen injection. Collagen was prepared by making a 4 mg/mL solution in 0.01 N acetic acid. Equal volumes of collagen and Freund's incomplete adjuvant, were emulsified by hand mixing until a bead of this material held its form when placed in water. Each animal received 300 μL of the mixture each time spread over 3 sites on back.

Calipering of normal (pre-disease) right and left ankle joints were done on day 9. On days 10-12, onset of arthritis occurred.

Rats were weighed on days (-) 1, 6, 9, 10, 11, 12, 13, 14, 15, 16, 17, 18, 19, and 20 of the study and caliper measurements of ankles taken every day beginning on day 9. Final body weights were taken on day 20. After final body weight measurement, animals were anesthetized for terminal plasma collection and then euthanized.

Both hind paws and knees were removed. Hind paws were weighed, placed (with knees) in formalin and then processed for microscopy.

Processing of Joints

Following 1-2 days in fixative and then 4-5 days in decalcifier, the ankle joints were cut in half longitudinally, knees were cut in half in the frontal plane, processed, embedded, sectioned and stained with toluidine blue.

Compound A demonstrated significant inhibition compared to controls receiving no treatment of ankle inflammation and ankle histopathology at doses tested (3.0 mg/kg, 10.0 mg/kg and 30.0 mg/kg).

Example H

Induction of Colitis in HLA-B27 Rats

The efficacy of the compounds of the present invention in reversing colitis was determined in HLA-B27 transgenic rats. HLA-B27 transgenic rats have been utilized as an animal model of Inflammatory Bowel Disease which mimics Crohn's Disease in humans. The rats overexpress the human MHC class I HLA-B27 heavy chain and beta-2 microglobulin proteins, which induces a variety of autoimmune diseases that include inflammation of the colon.

The therapeutic effect of Compound A of this invention in resolving colitis was evaluated in HLA-B27 transgenic rats. Diseased rats were dosed subcutaneously with 100 mg/kg of Compound A of this invention twice a day for 16 days. Animal samples dosed with 100 mg/kg of Compound A of this invention showed clinical and histological resolution of colitis and mimicked similar efficacy with the positive control group treated with anti-alpha4 antibody GG5/3.

Disease Activity Index (DAI) scores indicated overall improved scores for rats dosed with 100 mg/kg of Compound A of this invention and 10 mg/kg of GG5/3 (positive control) than rats dosed with vehicle. Fecal consistency and FOB scores for rats dosed with Compound A and GG5/3 were statistically different from the vehicle group.

Induction of Colitis

20 HLA-B27 (6-9 weeks old) transgenic rats were ordered from Taconic. Rats acclimated in animal facility for 10 weeks. Animal bedding was mixed from different cages once a week to control for a "dirty" environmental flora.

Treatments

Rats were enrolled and randomized into four groups (n=5) based on weight and DAI scores (FC≧3, FOB≧2). The experimental groups were dosed subcutaneously with Compound A 100 mg/kg (pH 2.8) twice a day for 16 days and terminated at trough. The control groups included a vehicle-treated (pH 3.2) group and a GG5/3 (mouse anti-rat alpha-4 integrin antibody) positive control group dosed subcutaneously at 10 mg/kg (5 mL/kg) on d0, d3, and d6 and terminated at trough on d8 (Table H1). Compound A and vehicle treatments were formulated every 5 days.

TABLE H1

Study Design for IBD.

| Treatment | N | Dose (mg/kg/day) | Dose Vol. (mL/kg) | Route | Frequency | Formulation |
|---|---|---|---|---|---|---|
| Vehicle | 5 | 0 | 0 | SC | b.id | 0.9% Saline, pH 3.3 with 10N NaOH |
| Compound A | 5 | 100 | 5 | SC | b.id | 0.9% Saline, pH 2.8 with 10N NaOH |
| GG5/3 | 5 | 30 | 5 | SC | Day 0, 3, & 6 | 1x PBS |

SC = subcutaneous

Endpoint Read-Outs

Disease Activity Index scores, Fecal Consistency test and Fecal Occult Blood test, were taken 4 times a week to generate in-life clinical scores. The primary read-out for the study was a histopathological analysis of cecum, proximal colon, mid-colon, and distal colon. An IBD scoring system was applied (Table H2).

TABLE H2

| | IBD Scoring System Multiple Endpoints |
|---|---|
| A | Destruction of epithelium and glands |
| B | Dilatation of glandular crypts |
| C | Depletion and loss of goblet cells |
| D | Inflammatory cell infiltrates |
| E | Edema |
| F | Vascular congestion |
| G | Crypt Abscesses |
| H | Atrophia |

Disease Activity Index (DAI) scores were lower for rats dosed with Compound A and GG5/3 (positive control) than the vehicle group. Fecal Consistency and Fecal Occult Blood Test AUC scores for Compound A and GG5/3 (positive control) dose groups were also statistically different from the vehicle.

While some embodiments of the invention have been illustrated and described, it will be appreciated that various changes can be made therein without departing from the spirit and scope of the invention.

What is claimed is:

1. A method for treating a disease in a patient said disease selected from the group consisting of asthma, inflammatory bowel disease, ulcerative colitis, Crohn's disease, multiple sclerosis, rheumatoid arthritis, tumor metastasis, graft versus host disease, and organ or tissue rejection, which method comprises administering to the patient a pharmaceutical composition comprising a pharmaceutically acceptable carrier and a therapeutically effective amount of one or more of a compound of formula I:

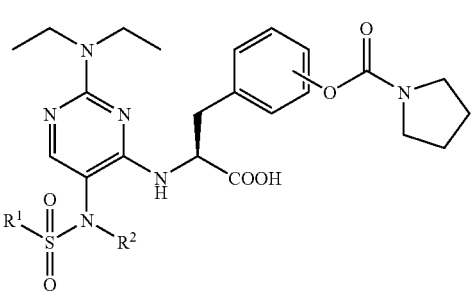

wherein:
$R^1$ is selected from the group consisting of $C_1$ to $C_4$ alkyl and $C_1$ to $C_4$ haloalkyl; and
$R^2$ is selected from the group consisting of $C_1$ to $C_4$ alkyl, $C_2$ to $C_4$ alkenyl, $C_2$ to $C_4$ alkynyl, and $C_3$-$C_6$ cycloalkyl
or a pharmaceutically acceptable salt or ester of the —COOH group thereof.

2. The method of claim 1, wherein the disease is asthma.

3. The method of claim 1 wherein the disease is Crohn's disease.

4. The method of claim 1, wherein the disease is rheumatoid arthritis.

5. The method of claim 1, wherein $R^1$ is $C_1$ to $C_2$ alkyl.

6. The method of claim 1, wherein $R^1$ is methyl or trifluoromethyl.

7. The method of claim 1, wherein $R^1$ is methyl.

8. The method of claim 1, wherein $R^2$ is $C_1$ to $C_4$ alkyl.

9. The method of claim 1, wherein $R^2$ is $C_1$ to $C_3$ alkyl.

10. The method of claim 9, wherein $R^2$ is methyl or ethyl.

11. The method of claim 9, wherein $R^2$ is isopropyl.

12. The method of claim 1, wherein $R^2$ is $C_3$ to $C_6$ cycloalkyl.

13. The method of claim 12, wherein $R^2$ is cyclopentyl.

14. The method of claim 1, wherein $R^2$ is $C_2$ to $C_4$ alkenyl.

15. The method of claim 14, wherein $R^2$ is allyl.

16. The method of claim 1, wherein $R^2$ is $C_2$ to $C_4$ alkynyl.

17. The method of claim 16, wherein $R^2$ is propargyl.

18. The method of claim 1, wherein the compound is selected from the group consisting of:

(S)-2-(2-(diethylamino)-5-(N-ethyl-1,1,1-trifluoromethylsulfonamido)pyrimidin-4-ylamino)-3-(4-(pyrrolidine-1-carbonyloxy)phenyl)propanoic acid;

(S)-2-(2-(diethylamino)-5-(N-isopropylmethylsulfonamido)pyrimidin-4-ylamino)-3-(4-(pyrrolidine-1-carbonyloxy)phenyl)propanoic acid;

(S)-2-(5-(N-cyclopentylmethylsulfonamido)-2-(diethylamino)pyrimidin-4-ylamino)-3-(4-(pyrrolidine-1-carbonyloxy)phenyl)propanoic acid;

(S)-2-(2-(diethylamino)-5-(N-methylmethylsulfonamido)pyrimidin-4-ylamino)-3-(4-(pyrrolidine-1-carbonyloxy)phenyl)propanoic acid;

(S)-2-(2-(diethylamino)-5-(N-(prop-2-ynyl)methylsulfonamido)pyrimidin-4-ylamino)-3-(4-(pyrrolidine-1-carbonyloxy)phenyl)propanoic acid;

(S)-2-(2-(diethylamino)-5-(N-ethylmethylsulfonamido)pyrimidin-4-ylamino)-3-(4-(pyrrolidine-1-carbonyloxy)phenyl)propanoic acid;

(S)-2-(5-(N-allylmethylsulfonamido)-2-(diethylamino)pyrimidin-4-ylamino)-3-(4-(pyrrolidine-1-carbonyloxy)phenyl)propanoic acid; (S)-2-(2-(diethylamino)-5-(N-ethylbutylsulfonamido)pyrimidin-4-ylamino)-3-(4-(pyrrolidine-1-carbonyloxy)phenyl)-propanoic acid;

(S)-2-(5-(3-chloro-N-ethylpropylsulfonamido)-2-(diethylamino)-pyrimidin-4-ylamino)-3-(4-(pyrrolidine-1-carbonyloxy)phenyl)propanoic acid;

(S)-2-(5-(3-chloro-N-methylpropyl-sulfonamido)-2-(diethylamino)pyrimidin-4-ylamino)-3-(4-(pyrrolidine-1-carbonyloxy)phenyl)propanoic acid;

(S)-2-(2-(diethylamino)-5-(N-ethyl-3,3,3-trifluoropropylsulfonamido)-pyrimidin-4-ylamino)-3-(4-(pyrrolidine-1-carbonyloxy)phenyl)propanoic acid;

(S)-2-(2-(diethylamino)-5-(N-ethylpropylsulfonamido)pyrimidin-4-ylamino)-3-(4-(pyrrolidine-1-carbonyloxy)phenyl)-propanoic acid; and (S)-2-(2-(diethylamino)-5-(N-ethyl-2-methylpropylsulfonamido)pyrimidin-4-ylamino)-3-(4-(pyrrolidine-1-carbonyloxy)-phenyl)propanoic acid;

and pharmaceutically acceptable salts or esters, thereof.

19. The method of claim 1, wherein the disease is multiple sclerosis.

20. The method of claim 1, wherein the disease is tumor metastasis.

21. The method of claim 1, wherein the disease is graft versus host disease.

22. The method of claim 1, wherein the disease is organ or tissue rejection.

23. The method of claim 1, wherein the disease is ulcerative colitis.

24. The method of claim 1, wherein the disease is inflammatory bowel disease.

* * * * *